US007390643B2

(12) United States Patent
Croteau et al.

(10) Patent No.: US 7,390,643 B2
(45) Date of Patent: Jun. 24, 2008

(54) GERANYL DIPHOSPHATE SYNTHASE MOLECULES, AND NUCLEIC ACID MOLECULES ENCODING SAME

(75) Inventors: Rodney Bruce Croteau, Pullman, WA (US); Charles Cullen Burke, Moscow, ID (US)

(73) Assignee: Washington State University Research Foundation, Pullman, WA (US)

( * ) Notice: Subject to any disclaimer, the term of this patent is extended or adjusted under 35 U.S.C. 154(b) by 253 days.

(21) Appl. No.: 11/047,828

(22) Filed: Jan. 31, 2005

(65) Prior Publication Data

US 2005/0204417 A1 Sep. 15, 2005

Related U.S. Application Data

(63) Continuation of application No. PCT/US03/23159, filed on Jul. 23, 2003.

(60) Provisional application No. 60/400,081, filed on Jul. 31, 2002.

(51) Int. Cl.
*C12N 5/14* (2006.01)
*C12N 5/10* (2006.01)
*C12N 1/21* (2006.01)
*C12N 15/00* (2006.01)
*C07H 21/00* (2006.01)
*C07K 14/00* (2006.01)
*C12P 21/00* (2006.01)
*C12N 9/10* (2006.01)
*C12Q 1/48* (2006.01)

(52) U.S. Cl. ............... 435/196; 435/252.3; 435/325; 435/419; 435/69.1; 435/320.1; 435/15; 530/350; 536/23.2

(58) Field of Classification Search ............... 435/69.1, 435/320.1, 252.3, 325, 471, 419, 193, 15; 530/350; 536/23.2
See application file for complete search history.

(56) References Cited

U.S. PATENT DOCUMENTS

| 4,472,833 | A | 9/1984 | Turrell et al. |
| 5,680,510 | A | 10/1997 | Hon et al. |
| 5,751,905 | A | 5/1998 | Chen et al. |
| 5,876,964 | A | 3/1999 | Croteau et al. |
| 6,043,072 | A | 3/2000 | Croteau et al. |
| 6,303,330 | B1 | 10/2001 | Croteau et al. |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Current Protocols in Molecular Biology, Hybridization Analysis of DNA Blots, pp. 2.10.8-2.10.11, 1993.*
Kappel et al., Current Opinion in Biotechnology 3:548-553, 1992.*
Mullins et al., Hypertension 22(4):630-633, 1993.*
Mullins et al., J. Clin. Invest. 97(7):1557-1560, 1996.*
Wigley et al., Reprod. Fert. Dev. 6:585-588, 1994.*
Cameron, E., Molecular Biotechnology 7:253-265, 1997.*
"Electronic Plant Gene Register, The," *Plant Physiology* 108(3):1341-1343, Jul. 1995 (Plant Gene Register PGR95-018).
"Electronic Plant Gene Register, The," *Plant Physiology* 110(1):336, Jan. 1996 (Plant Gene Register PGR95-119).
Aitken, S.M., et al., "A cDNA Encoding Geranylgeranyl Pyrophosphate Synthase From White Lupin," *Plant Physiology.* 108:837-838, 1995.
Bantignies, B., et al., "Nucleotide Sequence of a *Catharanthus roseus* Geranylgeranyl Pyrophosphate Synthase Gene (Accession No. X92893) (PGR95-119)," *Plant Physiology* 110:336, 1995.
Bonk, M., et al., "Chloroplast Import of Four Carotenoid Biosynthetic Enzymes In Vitro Reveals Differential Fates Prior to Membrane Binding and Oligomeric Assembly," *Eur. J. Biochem.* 247:942-950, 1997.
Bouvier, F., et al., "Molecular Cloning of Geranyl Diphosphate Synthase and Compartmentation of Monoterpene Synthesis in Plant Cells," *The Plant Journal* 24(2):241-252, 2000.
Buckel, P., "Recombinant Proteins for Therapy," *Trends in Pharmacological Science* 17:450-456, 1996.
Burke, C., and R. Croteau, "Interaction With the Small Subunit of Geranyl Diphosphate Synthase Modifies the Chain Length Specificity of Geranylgeranyl Diphosphate Synthase to Produce Geranyl Diphosphate," *The Journal of Biological Chemistry* 277(5):3141-3149, Feb. 1, 2002.
Burke, C.C. et al., "Geranyl Diphosphate Synthase: Cloning, Expression, and Characterization of This Prenyltransferase as a Heterodimer," *Proc. Natl. Acad. Sci. USA* 96(23):13062-13067, Nov. 1999.
Chen, A., et al., "Isoprenyl Diphosphate Synthases: Protein Sequence Comparisons, a Phylogenetic Tree, and Predictions of Secondary Structure," *Protein Science* 3:600-607, 1994.
Clastre, M., et al., "Purification and Characterization of Geranyl Diphosphate Synthase From *Vitis vinifera* L. cv Muscat de Frontignan Cell Cultures," *Plant Physiology* 102:205-211, 1993.
Croteau, R., and P.T. Purkett, "Geranyl Pyrophosphate, Synthase: Characterization of the Enzyme and Evidence That This Chain-Length Specific Prenyltransferase Is Associated With Monoterpene Biosynthesis in Sage (*Salvia officinalis*)," *Archives of Biochemistry and Biophysics* 271(2):524-535, Jun. 1989.

(Continued)

*Primary Examiner*—Delia M Ramirez
(74) *Attorney, Agent, or Firm*—Christensen O'Connor Johnson Kindness PLLC

(57) ABSTRACT

In one aspect, the present invention provides isolated nucleic acid molecules that each encode a geranyl diphosphate synthase protein, wherein each isolated nucleic acid molecule hybridizes to a nucleic acid molecule consisting of the sequence set forth in SEQ ID NO:1 under conditions of 5×SSC at 45° C. for one hour. The present invention also provides isolated geranyl diphosphate synthase proteins, and methods for altering the level of expression of geranyl diphosphate synthase protein in a host cell.

14 Claims, 1 Drawing Sheet

OTHER PUBLICATIONS

Endo, T., and T. Suga, "Demonstration of Geranyl Diphosphate Synthase in Several Higher Plants," *Phytochemistry* 31(7):2273-2275, 1992.

Forster, B.P., et al., "Genetic Engineering of Crop Plants: From Genome to Gene," *Expl. Agric.* 33:15-33, 1997.

Heide, L., and U. Berger, "Partial Purification and Properties of Geranyl Pyrophosphate Synthase From *Lithospermum erythrorhizon* Cell Cultures," *Archives of Biochemistry and Biophysics* 273(2):331-338, Sep. 1989.

Koh, S.N., et al., "A Speech Synthesizer for Mandarin Chinese," *IEEE Transactions on Consumer Electronics* 36(4):912-917, Nov. 1990.

Kuntz, M., et al., "Identification of a cDNA for the Plastid-Located Geranylgeranyl Pyrophosphate Synthase From *Capsicum annuum*: Correlative Increase in Enzyme Activity and Transcript Level During Fruit Ripening," *The Plant Journal* 2(1):25-34, 1992.

Ledley, F.D., "Pharmaceutical Approach to Somatic Gene Therapy," *Pharmaceutical Research* 13(11):1595-1614, 1996.

Lee, L., et al., "Improved Tone Concatenation Rules in a Formant-Based Chinese Text-to-Speech System," *IEEE Transactions on Speech and Audio Processing* 1(3):287-294, Jul. 1993.

Pompon, D., et al., "Yeast Expression of Animal and Plant P450s in Optimized Redox Environments," *Methods in Enzymology* 272:51-64, 1996.

Poulter, C.D., and H.C. Rilling, "The Prenyl Transfer Reaction. Enzymatic and Mechanistic Studies of the 1'-4 Coupling Reaction in the Terpene Biosynthetic Pathway," *Accounts of Chemical Research* 11:307-313, 1978.

Roth, J.A., and R.J. Cristiano, "Gene Therapy for Cancer: What Have We Done and Where Are We Going?" *Journal of the National Cancer Institute* 89(1):21-39, Jan. 1, 1997.

Schmid, S.L., and H. Damke, "Coated Vesicles: A Diversity of Form and Function," *The FASEB Journal* 9(14):1445-1453, Nov. 1995.

Scolnik, P.A., and G.E. Bartley, "Nucleotide Sequence of an *Arabidopsis* cDNA for Geranylgeranyl Pyrophosphate Synthase," *Plant Physiology* 104:1469-1470, 1994.

Scolnik, P.A., and G.E. Bartley, "A Table of Some Cloned Plant Genes Involved in Isoprenoid Biosynthesis," *Plant Molecular Biology Reporter* 14(4):305-319, 1996.

Sheldon, K., et al., "Loligomers: Design of De Novo Peptide-Based Intracellular Vehicles," *Proc. Natl. Acad. Sci. USA* 92(6):2056-2060, Mar. 14, 1995.

Suga, T., and T. Endo, "Geranyl Diphosphate Synthase in Leaves of *Pelargonium roseum*," *Phytochemistry* 30(6):1757-1761, 1991.

Sutcliffe, J.G., "Complete Nucleotide Sequence of the *Escherichia coli* Plasmid pBR322," *Cold Spring Harbor Symposia on Quantitative Biology* 43:77-90, 1979.

Tholl, D., et al., "Partial Purification and Characterization of the Short-Chain Prenyltransferases, Geranyl Diphospate Synthase and Farnesyl Diphosphate Synthase, From *Abies grandis* (Grand Fir)," *Archives of Biochemistry and Biophysics* 386(2):233-242, Feb. 15, 2001.

Wearley, L.L., "Recent Progress in Protein and Peptide Delivery by Noninvasive Routes," *Critical Reviews in Therapeutic Drug Carrier Systems* 8(4):331-394, 1991.

Zhu, X., et al., "Cloning and Functional Expression of a Novel Geranylgeranyl Pyrophosphate Synthase Gene From *Arabidopsis thaliana* in *Escherichia coli*," *Plant Cell Physiology* 38(3):357-361, 1997.

Zhu, X., et al., "Geranylgeranyl Pyrophosphate Synthase Encoded by the Newly Isolated Gene GGPS6 From *Arabidopsis thaliana* Is Localized in Mitochondria," *Plant Molecular Biology* 35:331-341, 1997.

Burke, C., and R. Croteau, "Geranyl Diphosphate Synthase From *Abies grandis*: cDNA Isolation, Functional Expression, and Characterization," Archives of Biochemistry and Biophysics 405:130-136, 2002.

\* cited by examiner

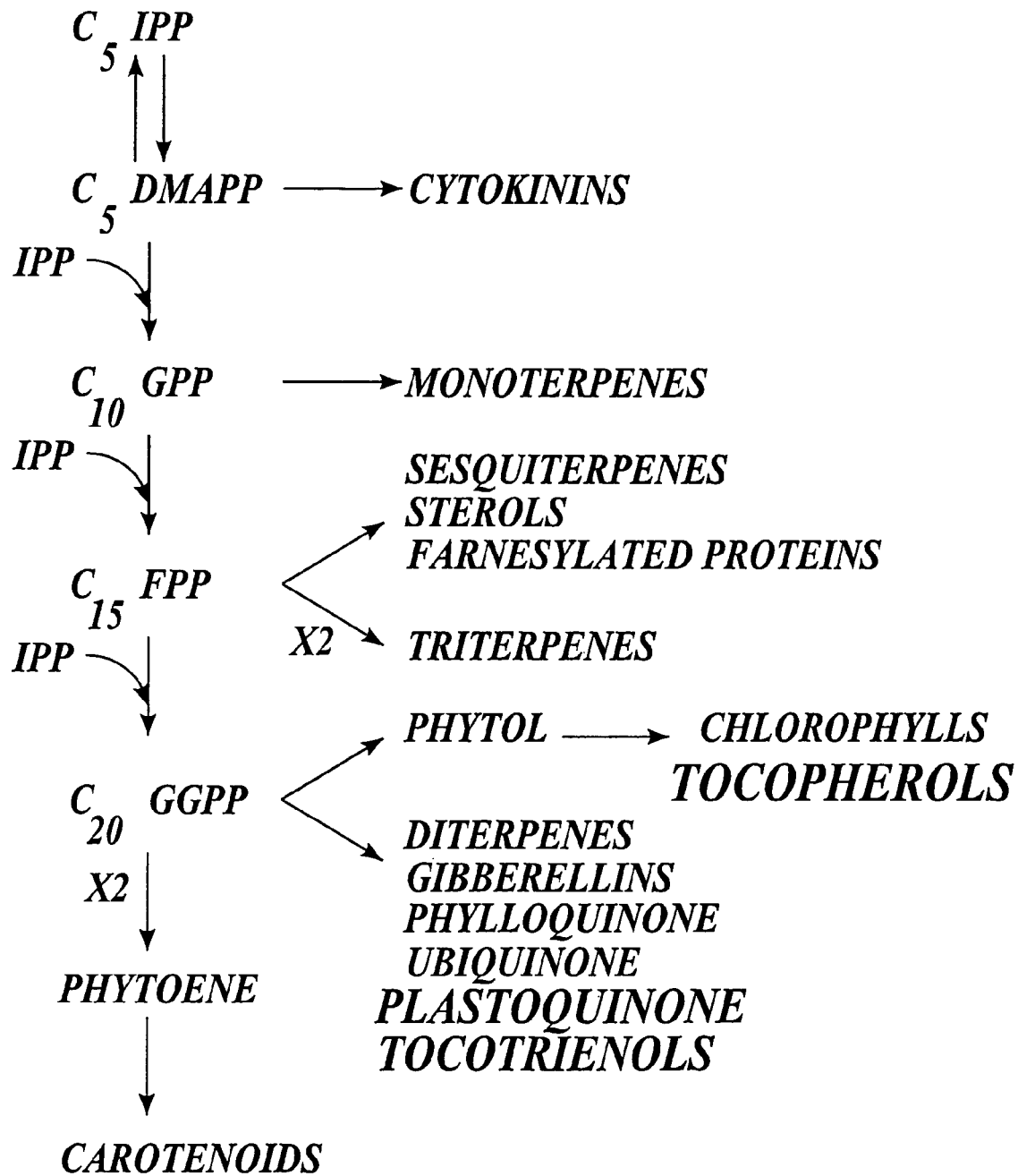
(PRIOR ART)

SEQUENCE LISTING

```
<160> NUMBER OF SEQ ID NOS: 42

<210> SEQ ID NO 1
<211> LENGTH: 1093
<212> TYPE: DNA
<213> ORGANISM: Abies Grandis

<400> SEQUENCE: 1
tcactggatc gaagcaagat aactctccct tagctctgtt caacaattca tcagaaaact      60
cctttgcttt ctccaaaccc atgagctttg gataagttgc cttatcacta atcaaatcct     120
ttcctgcagt cttgcccagt tcgtctgatg atttcgtgac atcgagtatg tcatccacaa     180
cctgaaaaag aagccccacg caacgggcat accttcgagc tctctcgatc acaatctccg     240
aagcaccacc gatgatcgcc ccacacacaa ccgagcactc caagagcatt gcagtcttgt     300
gaatatgaat ccattccaga gtctgaaggt caatagaagg atcccttcg ctggcaatat      360 cgaccatctg gccacccata accccttcag agcctgttgc tctacccagt tcagatacca    420
tcctcaaaat cctatcagcc cccacagttt tgcttgtgga aactgcaata tgctcaaagg    480
cgtaagaatg aagcgcattc cctgcagtaa cagcagtatc ttccccgaag atcttatggt    540
ttgtaggttt ccctcgccgt aaatcatcat tgtctatgca aggcaagtca tcatgcatca    600
aagacattgt gtggatcatt tcgattgcac aggcagttgg aatcgcaagc tcctcggttc    660
ctccaacaag ctcacatgct gcaatgcaca gaacaggacg aactcgtttc cctcctgcca    720
gaagagaata cctcatggat tcatatattt tctggggata acgaagtggg atagccttat    780
tcaacgcctc attcactgtc attgccttgg aatccatgta cttgttgaaa tcaaattcaa    840
cggccttctt cccttttttgt ggaggattaa gcaactgggc aactgtagcg tttgaggatc    900
tagatgccgg attttatat gaagatagct tcctcttcga ataccctcgg aggaggccca    960
tatgctcgcc attaaaagct tccagtgagg ttgaagctcc atgaaaaggt tttaatgggc  1020
tggtaggatg cagggtatgg cagctagctg ccataccatt gtaacccatg gttgccatag  1080
cactgtaagc cat                                                     1093

<210> SEQ ID NO 2
<211> LENGTH: 1524
<212> TYPE: DNA
<213> ORGANISM: Abies Grandis
<220> FEATURE:
<221> NAME/KEY: CDS
<222> LOCATION: (122)..(1264)
```

<400> SEQUENCE: 2

```
gattttccct gctacaaaaa tctatgtatt gtttcttcag ttgcattcaa agatctatag      60
aatttcgagc tttgaatttg ttttaagagt ttatagcagg agctaatcat ataaagagga     120 c atg gct tac agt gct atg gca acc atg ggt tac aat ggt atg gca gct    169
  Met Ala Tyr Ser Ala Met Ala Thr Met Gly Tyr Asn Gly Met Ala Ala
  1               5                  10                  15 agc tgc cat acc ctg cat cct acc agc cca tta aaa cct ttt cat gga      217
Ser Cys His Thr Leu His Pro Thr Ser Pro Leu Lys Pro Phe His Gly
            20                  25                  30 gct tca acc tca ctg gaa gct ttt aat ggc gag cat atg ggc ctc ctc      265
Ala Ser Thr Ser Leu Glu Ala Phe Asn Gly Glu His Met Gly Leu Leu
        35                  40                  45 cga ggg tat tcg aag agg aag cta tct tca tat aaa aat ccg gca tct      313
Arg Gly Tyr Ser Lys Arg Lys Leu Ser Ser Tyr Lys Asn Pro Ala Ser
    50                  55                  60 aga tcc tca aac gct aca gtt gcc cag ttg ctt aat cct cca caa aaa      361
Arg Ser Ser Asn Ala Thr Val Ala Gln Leu Leu Asn Pro Pro Gln Lys
65                  70                  75                  80 ggg aag aag gcc gtt gaa ttt gat ttc aac aag tac atg gat tcc aag      409
Gly Lys Lys Ala Val Glu Phe Asp Phe Asn Lys Tyr Met Asp Ser Lys
                85                  90                  95 gca atg aca gtg aat gag gcg ttg aat aag gct atc cca ctt cgt tat      457
Ala Met Thr Val Asn Glu Ala Leu Asn Lys Ala Ile Pro Leu Arg Tyr
            100                 105                 110 ccc cag aaa ata tat gaa tcc atg agg tat tct ctt ctg gca gga ggg      505
Pro Gln Lys Ile Tyr Glu Ser Met Arg Tyr Ser Leu Leu Ala Gly Gly
        115                 120                 125 aaa cga gtt cgt cct gtt ctg tgc att gca gca tgt gag ctt gtt gga      553
Lys Arg Val Arg Pro Val Leu Cys Ile Ala Ala Cys Glu Leu Val Gly
    130                 135                 140 gga acc gag gag ctt gcg att cca act gcc tgt gca atc gaa atg atc      601
Gly Thr Glu Glu Leu Ala Ile Pro Thr Ala Cys Ala Ile Glu Met Ile
145                 150                 155                 160 cac aca atg tct ttg atg cat gat gac ttg cct tgc ata gac aat gat      649
His Thr Met Ser Leu Met His Asp Asp Leu Pro Cys Ile Asp Asn Asp
                165                 170                 175 gat tta cgg cga ggg aaa cct aca aac cat aag atc ttc ggg gaa gat      697
Asp Leu Arg Arg Gly Lys Pro Thr Asn His Lys Ile Phe Gly Glu Asp
            180                 185                 190 act gct gtt act gca ggg aat gcg ctt cat tct tac gcc ttt gag cat      745
Thr Ala Val Thr Ala Gly Asn Ala Leu His Ser Tyr Ala Phe Glu His
        195                 200                 205 att gca gtt tcc aca agc aaa act gtg ggg gct gat agg att ttg agg      793
Ile Ala Val Ser Thr Ser Lys Thr Val Gly Ala Asp Arg Ile Leu Arg
    210                 215                 220 atg gta tct gaa ctg ggt aga gca aca ggc tct gaa ggg gtt atg ggt      841
Met Val Ser Glu Leu Gly Arg Ala Thr Gly Ser Glu Gly Val Met Gly
225                 230                 235                 240 ggc cag atg gtc gat att gca agc gaa ggg gat cct tct att gac ctt      889
Gly Gln Met Val Asp Ile Ala Ser Glu Gly Asp Pro Ser Ile Asp Leu
                245                 250                 255 cag act ctg gaa tgg att cat att cac aag act gca atg ctc ttg gag      937
Gln Thr Leu Glu Trp Ile His Ile His Lys Thr Ala Met Leu Leu Glu
            260                 265                 270 tgc tcg gtt gtg tgt ggg gcg atc atc ggt ggt gct tcg gag att gtg      985
Cys Ser Val Val Cys Gly Ala Ile Ile Gly Gly Ala Ser Glu Ile Val
        275                 280                 285 atc gag aga gct cga agg tat gcc cgt tgc gtg ggg ctt ctt ttt cag     1033
Ile Glu Arg Ala Arg Arg Tyr Ala Arg Cys Val Gly Leu Leu Phe Gln
```

```
Ile Glu Arg Ala Arg Arg Tyr Ala Arg Cys Val Gly Leu Leu Phe Gln
    290                 295                 300 gtt gtg gat gac ata ctc gat gtc acg aaa tca tca gac gaa ctg ggc      1081
Val Val Asp Asp Ile Leu Asp Val Thr Lys Ser Ser Asp Glu Leu Gly
305                 310                 315                 320 aag act gca gga aag gat ttg att agt gat aag gca act tat cca aag      1129
Lys Thr Ala Gly Lys Asp Leu Ile Ser Asp Lys Ala Thr Tyr Pro Lys
                325                 330                 335 ctc atg ggt ttg gag aaa gca aag gag ttt tct gat gaa ttg ttg aac      1177
Leu Met Gly Leu Glu Lys Ala Lys Glu Phe Ser Asp Glu Leu Leu Asn
            340                 345                 350 aga gct aag gga gag tta tct tgc ttc gat cca gtg aag gca gca cct      1225
Arg Ala Lys Gly Glu Leu Ser Cys Phe Asp Pro Val Lys Ala Ala Pro
        355                 360                 365 ctg ttg ggt ctt gca gat tac gtg gca ttc aga caa aat tgaagagcct       1274
Leu Leu Gly Leu Ala Asp Tyr Val Ala Phe Arg Gln Asn
    370                 375                 380 cctcaaagcg ttcttgtttg ttagagtgga taatcttggt ttaatagttt tttaaagtaa    1334
cagagttaga cctgcgttcc ctgccctccg tatactatct atgatgtagc actgcaactt    1394
cttgtattgt gaaaacttga gcacagcatt ttaattgtga aatctagtcc aactgcaaac    1454
tcaaaccgga tattcagtcg atggcccgtc tacaggccga ctggccgtga ttcaaggcga    1514
gcaatactca                                                           1524

<210> SEQ ID NO 3
<211> LENGTH: 381
<212> TYPE: PRT
<213> ORGANISM: Abies Grandis

<400> SEQUENCE: 3

Met Ala Tyr Ser Ala Met Ala Thr Met Gly Tyr Asn Gly Met Ala Ala
1               5                   10                  15

Ser Cys His Thr Leu His Pro Thr Ser Pro Leu Lys Pro Phe His Gly
                20                  25                  30

Ala Ser Thr Ser Leu Glu Ala Phe Asn Gly Glu His Met Gly Leu Leu
            35                  40                  45

Arg Gly Tyr Ser Lys Arg Lys Leu Ser Ser Tyr Lys Asn Pro Ala Ser
        50                  55                  60

Arg Ser Ser Asn Ala Thr Val Ala Gln Leu Leu Asn Pro Pro Gln Lys
65                  70                  75                  80

Gly Lys Lys Ala Val Glu Phe Asp Phe Asn Lys Tyr Met Asp Ser Lys
                85                  90                  95

Ala Met Thr Val Asn Glu Ala Leu Asn Lys Ala Ile Pro Leu Arg Tyr
            100                 105                 110

Pro Gln Lys Ile Tyr Glu Ser Met Arg Tyr Ser Leu Leu Ala Gly Gly
        115                 120                 125

Lys Arg Val Arg Pro Val Leu Cys Ile Ala Ala Cys Glu Leu Val Gly
130                 135                 140

Gly Thr Glu Glu Leu Ala Ile Pro Thr Ala Cys Ala Ile Glu Met Ile
145                 150                 155                 160

His Thr Met Ser Leu Met His Asp Asp Leu Pro Cys Ile Asp Asn Asp
                165                 170                 175

Asp Leu Arg Arg Gly Lys Pro Thr Asn His Lys Ile Phe Gly Glu Asp
            180                 185                 190

Thr Ala Val Thr Ala Gly Asn Ala Leu His Ser Tyr Ala Phe Glu His
        195                 200                 205
```

```
Ile Ala Val Ser Thr Ser Lys Thr Val Gly Ala Asp Arg Ile Leu Arg
    210                 215                 220

Met Val Ser Glu Leu Gly Arg Ala Thr Gly Ser Glu Gly Val Met Gly
225                 230                 235                 240

Gly Gln Met Val Asp Ile Ala Ser Glu Gly Asp Pro Ser Ile Asp Leu
                245                 250                 255

Gln Thr Leu Glu Trp Ile His Ile His Lys Thr Ala Met Leu Leu Glu
            260                 265                 270

Cys Ser Val Val Cys Gly Ala Ile Ile Gly Gly Ala Ser Glu Ile Val
        275                 280                 285

Ile Glu Arg Ala Arg Arg Tyr Ala Arg Cys Val Gly Leu Leu Phe Gln
    290                 295                 300

Val Val Asp Asp Ile Leu Asp Val Thr Lys Ser Ser Asp Glu Leu Gly
305                 310                 315                 320

Lys Thr Ala Gly Lys Asp Leu Ile Ser Asp Lys Ala Thr Tyr Pro Lys
                325                 330                 335

Leu Met Gly Leu Glu Lys Ala Lys Glu Phe Ser Asp Glu Leu Leu Asn
            340                 345                 350

Arg Ala Lys Gly Glu Leu Ser Cys Phe Asp Pro Val Lys Ala Ala Pro
        355                 360                 365

Leu Leu Gly Leu Ala Asp Tyr Val Ala Phe Arg Gln Asn
    370                 375                 380

<210> SEQ ID NO 4
<211> LENGTH: 1289
<212> TYPE: DNA
<213> ORGANISM: Abies Grandis
<220> FEATURE:
<221> NAME/KEY: CDS
<222> LOCATION: (83)..(1231)

<400> SEQUENCE: 4
gtgcgctgtt caatgcaacg atcaatatta gaatcaccag agttgatagc aggaaccatt      60
aaaacagaaa tagaacaaag at atg gct tac agt tgt atg gca gct agc tgc     112
                         Met Ala Tyr Ser Cys Met Ala Ala Ser Cys
                           1               5                  10 cat ggc ctg cat ttt atg aat att gct tct cag gaa tgt aat ttg aaa     160
His Gly Leu His Phe Met Asn Ile Ala Ser Gln Glu Cys Asn Leu Lys
                15                  20                  25 aga ggt att atc cca tca aaa cgt ctg cat gga att tca tcc tca ttg     208
Arg Gly Ile Ile Pro Ser Lys Arg Leu His Gly Ile Ser Ser Ser Leu
            30                  35                  40 tgg gct tct aat ggc ttc caa ggc cat ttg gaa agg gac tta tcg gca     256
Trp Ala Ser Asn Gly Phe Gln Gly His Leu Glu Arg Asp Leu Ser Ala
        45                  50                  55 tat aga cat ctg gta tca tca tcc aga tgc tta aac aca atc gcc atg     304
Tyr Arg His Leu Val Ser Ser Ser Arg Cys Leu Asn Thr Ile Ala Met
    60                  65                  70 ttg agt aat ctg tct gaa caa gca aag gaa aag gcc act gaa ttt gat     352
Leu Ser Asn Leu Ser Glu Gln Ala Lys Glu Lys Ala Thr Glu Phe Asp
75                  80                  85                  90 ttc aag gag tac ttg cat tcc aaa gca ata tca gtg aat gag gca ctg     400
Phe Lys Glu Tyr Leu His Ser Lys Ala Ile Ser Val Asn Glu Ala Leu
                95                 100                 105 gag agg gct gtc cca ctt cgc tat cct gaa aaa ata cat gaa gct atg     448
Glu Arg Ala Val Pro Leu Arg Tyr Pro Glu Lys Ile His Glu Ala Met
            110                 115                 120
```

```
agg tat tct ctt cta gca gga ggg aag cgg att cgt cct att ctg act    496
Arg Tyr Ser Leu Leu Ala Gly Gly Lys Arg Ile Arg Pro Ile Leu Thr
            125                 130                 135 att gca gca tgt gag ctt gtg gga ggg agt gag gag ctc gcc atg cca    544
Ile Ala Ala Cys Glu Leu Val Gly Gly Ser Glu Glu Leu Ala Met Pro
        140                 145                 150 act gcc tgt gca atg gag atg atc cac aca atg tct ttg att cat gat    592
Thr Ala Cys Ala Met Glu Met Ile His Thr Met Ser Leu Ile His Asp
155                 160                 165                 170 gat ttg cct tcc atg gac aat gat gat tta cgc cga ggt aag ctt aca    640
Asp Leu Pro Ser Met Asp Asn Asp Asp Leu Arg Arg Gly Lys Leu Thr
                175                 180                 185 aac cac aag gtc ttt ggc gaa ggc act gct gtt ctt gca ggg gat gca    688
Asn His Lys Val Phe Gly Glu Gly Thr Ala Val Leu Ala Gly Asp Ala
            190                 195                 200 ctt ctt tca ttt gca ttt gag cac att gca gtg tcc aca agg aaa act    736
Leu Leu Ser Phe Ala Phe Glu His Ile Ala Val Ser Thr Arg Lys Thr
        205                 210                 215 gtg gcg agt cat agg gtt ttg agg gtg gta tct gaa ttg ggt aag gca    784
Val Ala Ser His Arg Val Leu Arg Val Val Ser Glu Leu Gly Lys Ala
    220                 225                 230 ata ggc tct caa ggg gtt gct ggt ggg cag gtt gct gat att acc agt    832
Ile Gly Ser Gln Gly Val Ala Gly Gly Gln Val Ala Asp Ile Thr Ser
235                 240                 245                 250 gaa ggg gat cca tct gtt ggg ctt gag act ctc gaa tgg att cac att    880
Glu Gly Asp Pro Ser Val Gly Leu Glu Thr Leu Glu Trp Ile His Ile
                255                 260                 265 cac aag act gca gtg ctc ttg gag tgc gcc gtt gtg agt ggg gcg atc    928
His Lys Thr Ala Val Leu Leu Glu Cys Ala Val Val Ser Gly Ala Ile
            270                 275                 280 atc ggt ggc gct tca gag aat gaa att gag aga act gga agg tat gcc    976
Ile Gly Gly Ala Ser Glu Asn Glu Ile Glu Arg Thr Gly Arg Tyr Ala
        285                 290                 295 cgt tgc gtt ggg ctt ctg ttt cag gtt gtg gat gac ata ctc gat gtc   1024
Arg Cys Val Gly Leu Leu Phe Gln Val Val Asp Asp Ile Leu Asp Val
    300                 305                 310 acc aga tca tca gaa gaa ttg gga aag act gca gga aag gat ttg gtt   1072
Thr Arg Ser Ser Glu Glu Leu Gly Lys Thr Ala Gly Lys Asp Leu Val
315                 320                 325                 330 agt gat aag gcc act tat ccc aag ctg atg ggt ttg gag aaa gcg aag   1120
Ser Asp Lys Ala Thr Tyr Pro Lys Leu Met Gly Leu Glu Lys Ala Lys
                335                 340                 345 gaa ttt gct gat gaa ttg ttg gac aga gct aag gag gag tta tct tgc   1168
Glu Phe Ala Asp Glu Leu Leu Asp Arg Ala Lys Glu Glu Leu Ser Cys
            350                 355                 360 ttc aac cca gct aag gct gca cct ctg ttg ggt ctt gca gat tac att   1216
Phe Asn Pro Ala Lys Ala Ala Pro Leu Leu Gly Leu Ala Asp Tyr Ile
        365                 370                 375 gca tta aga cag aac tgaaaagcct gcgaaatgtg ttcttatgta tgccgtttgt   1271
Ala Leu Arg Gln Asn
    380 gcttttgctt ttgcatct                                               1289

<210> SEQ ID NO 5
<211> LENGTH: 383
<212> TYPE: PRT
<213> ORGANISM: Abies Grandis

<400> SEQUENCE: 5

Met Ala Tyr Ser Cys Met Ala Ala Ser Cys His Gly Leu His Phe Met
```

-continued

```
 1               5                  10                  15
Asn Ile Ala Ser Gln Glu Cys Asn Leu Lys Arg Gly Ile Ile Pro Ser
             20                  25                  30
Lys Arg Leu His Gly Ile Ser Ser Leu Trp Ala Ser Asn Gly Phe
             35                  40                  45
Gln Gly His Leu Glu Arg Asp Leu Ser Ala Tyr Arg His Leu Val Ser
             50                  55                  60
Ser Ser Arg Cys Leu Asn Thr Ile Ala Met Leu Ser Asn Leu Ser Glu
 65                  70                  75                  80
Gln Ala Lys Glu Lys Ala Thr Glu Phe Asp Phe Lys Glu Tyr Leu His
                 85                  90                  95
Ser Lys Ala Ile Ser Val Asn Glu Ala Leu Glu Arg Ala Val Pro Leu
                100                 105                 110
Arg Tyr Pro Glu Lys Ile His Glu Ala Met Arg Tyr Ser Leu Leu Ala
                115                 120                 125
Gly Gly Lys Arg Ile Arg Pro Ile Leu Thr Ile Ala Ala Cys Glu Leu
            130                 135                 140
Val Gly Ser Glu Glu Leu Ala Met Pro Thr Ala Cys Ala Met Glu
145                 150                 155                 160
Met Ile His Thr Met Ser Leu Ile His Asp Asp Leu Pro Ser Met Asp
                165                 170                 175
Asn Asp Asp Leu Arg Arg Gly Lys Leu Thr Asn His Lys Val Phe Gly
                180                 185                 190
Glu Gly Thr Ala Val Leu Ala Gly Asp Ala Leu Leu Ser Phe Ala Phe
            195                 200                 205
Glu His Ile Ala Val Ser Thr Arg Lys Thr Val Ala Ser His Arg Val
            210                 215                 220
Leu Arg Val Val Ser Glu Leu Gly Lys Ala Ile Gly Ser Gln Gly Val
225                 230                 235                 240
Ala Gly Gly Gln Val Ala Asp Ile Thr Ser Glu Gly Asp Pro Ser Val
                245                 250                 255
Gly Leu Glu Thr Leu Glu Trp Ile His Ile His Lys Thr Ala Val Leu
            260                 265                 270
Leu Glu Cys Ala Val Val Ser Gly Ala Ile Ile Gly Ala Ser Glu
            275                 280                 285
Asn Glu Ile Glu Arg Thr Gly Arg Tyr Ala Arg Cys Val Gly Leu Leu
            290                 295                 300
Phe Gln Val Val Asp Asp Ile Leu Asp Val Thr Arg Ser Ser Glu Glu
305                 310                 315                 320
Leu Gly Lys Thr Ala Gly Lys Asp Leu Val Ser Asp Lys Ala Thr Tyr
                325                 330                 335
Pro Lys Leu Met Gly Leu Glu Lys Ala Lys Glu Phe Ala Asp Glu Leu
                340                 345                 350
Leu Asp Arg Ala Lys Glu Glu Leu Ser Cys Phe Asn Pro Ala Lys Ala
            355                 360                 365
Ala Pro Leu Leu Gly Leu Ala Asp Tyr Ile Ala Leu Arg Gln Asn
            370                 375                 380
```

<210> SEQ ID NO 6
<211> LENGTH: 1298
<212> TYPE: DNA
<213> ORGANISM: Abies Grandis
<220> FEATURE:
<221> NAME/KEY: CDS
<222> LOCATION: (90)..(1250)

<400> SEQUENCE: 6

```
attgattcat acatatggta tcgaaattgg tgagagctat gtattagatt gattctaagg    60
tagacagcag gaacaaatat aggaactac atg gct tac agt ggt atg gta cgt    113
                                 Met Ala Tyr Ser Gly Met Val Arg
                                  1               5 agc ttc caa ggc gtg tat ttt atg gct gtt gct ctt gat cga aac cgt    161
Ser Phe Gln Gly Val Tyr Phe Met Ala Val Ala Leu Asp Arg Asn Arg
         10              15                  20 aat ctg aag aga att gac att cca tca aaa cgt ttt gat gga gtt tcg    209
Asn Leu Lys Arg Ile Asp Ile Pro Ser Lys Arg Phe Asp Gly Val Ser
 25              30                  35                  40 acc tca ttt gtg gct tgt aat ggc gag cat ctg ggc ctt ccc gta aat    257
Thr Ser Phe Val Ala Cys Asn Gly Glu His Leu Gly Leu Pro Val Asn
                 45                  50                  55 ttg aag aaa gag ttc tta tca tgc ata caa cgg gca tcg tcc tct aga    305
Leu Lys Lys Glu Phe Leu Ser Cys Ile Gln Arg Ala Ser Ser Ser Arg
             60                  65                  70 tcc tca aac aca atc gtc cag ttt gct aat ttg cct gaa caa ggg aag    353
Ser Ser Asn Thr Ile Val Gln Phe Ala Asn Leu Pro Glu Gln Gly Lys
         75                  80                  85 aag gtc gtt gaa ttt gat ttc aat aag tac atg ctt tcc aag gca atg    401
Lys Val Val Glu Phe Asp Phe Asn Lys Tyr Met Leu Ser Lys Ala Met
 90                  95                 100 gca gtg act gag gca ttg gat aag gct atc cca cat agt tat ccc cag    449
Ala Val Thr Glu Ala Leu Asp Lys Ala Ile Pro His Ser Tyr Pro Gln
105                 110                 115                 120 aaa ata cat gaa tcc atg agg tat tct ctt ctg gca ggg ggg aag cgc    497
Lys Ile His Glu Ser Met Arg Tyr Ser Leu Leu Ala Gly Gly Lys Arg
                125                 130                 135 gtt cgt cct gtt ctg tgc att gct gcg tgt gaa ctt gtg gga gga agg    545
Val Arg Pro Val Leu Cys Ile Ala Ala Cys Glu Leu Val Gly Gly Arg
            140                 145                 150 gag gag ctc gcc atg cca act gcc tgc gca atg gaa atg atc cac aca    593
Glu Glu Leu Ala Met Pro Thr Ala Cys Ala Met Glu Met Ile His Thr
        155                 160                 165 atg tct ttg att cat gat gac tta cct tgc atg gac aac gat gat tta    641
Met Ser Leu Ile His Asp Asp Leu Pro Cys Met Asp Asn Asp Asp Leu
170                 175                 180 cgg cga ggt aag cct aca aac cat aag gtc ttc ggc cag gac act gct    689
Arg Arg Gly Lys Pro Thr Asn His Lys Val Phe Gly Gln Asp Thr Ala
185                 190                 195                 200 ctt ctt gca ggg gat gca ctt cat gca ttt gcc ttt gag cac att gta    737
Leu Leu Ala Gly Asp Ala Leu His Ala Phe Ala Phe Glu His Ile Val
                205                 210                 215 gcc ttt aca agc aaa tct gtg ggg agt gat ggg att ttg agg gcg gtt    785
Ala Phe Thr Ser Lys Ser Val Gly Ser Asp Gly Ile Leu Arg Ala Val
            220                 225                 230 act gaa ttg gct aga gca aca ggc cct caa ggg att atg ggt ggc cag    833
Thr Glu Leu Ala Arg Ala Thr Gly Pro Gln Gly Ile Met Gly Gly Gln
        235                 240                 245 att gtc gat att gcg agc gag cgg gat gct ttt gtt gac ctt cag act    881
Ile Val Asp Ile Ala Ser Glu Arg Asp Ala Phe Val Asp Leu Gln Thr
250                 255                 260 ctg gaa tgg atc cat att cac aag act gcg gtg ctc ttc gag tgc gcg    929
Leu Glu Trp Ile His Ile His Lys Thr Ala Val Leu Phe Glu Cys Ala
265                 270                 275                 280 act gtg tgt ggg gcg atc atc gga ggt gct tcg ggg gat gaa att gag    977
Thr Val Cys Gly Ala Ile Ile Gly Gly Ala Ser Gly Asp Glu Ile Glu
```

```
                 285                  290                  295
aga att cga agg ttt gcc cgt tat ttg ggg ctt ctg ttt caa gtc gtg    1025
Arg Ile Arg Arg Phe Ala Arg Tyr Leu Gly Leu Leu Phe Gln Val Val
            300                  305                  310 gat gac ata ctc gat gtc aca aaa tct tct gaa gat ttg ggt aag act    1073
Asp Asp Ile Leu Asp Val Thr Lys Ser Ser Glu Asp Leu Gly Lys Thr
                315                  320                  325 gca gga aag gat ttg gtt agt gat aag gcc act tat ccc aag ctg atg    1121
Ala Gly Lys Asp Leu Val Ser Asp Lys Ala Thr Tyr Pro Lys Leu Met
        330                  335                  340 ggt tta gag aaa gca aag gga ttt tct ctt gaa ttg ttg aac aaa gct    1169
Gly Leu Glu Lys Ala Lys Gly Phe Ser Leu Glu Leu Leu Asn Lys Ala
    345                  350                  355                  360 aag gag gag tta tca tgc ttc gat cca atg aag gct gca cct ctg ttc    1217
Lys Glu Glu Leu Ser Cys Phe Asp Pro Met Lys Ala Ala Pro Leu Phe
                365                  370                  375 ggt ctt gca gat tac atg gca ctc aga cag aat tgaaaagcct agtaaaatcg  1270
Gly Leu Ala Asp Tyr Met Ala Leu Arg Gln Asn
        380                  385 ttcctacgta aaaaaaaaaa aaaaaaaa                                     1298

<210> SEQ ID NO 7
<211> LENGTH: 387
<212> TYPE: PRT
<213> ORGANISM: Abies Grandis

<400> SEQUENCE: 7

Met Ala Tyr Ser Gly Met Val Arg Ser Phe Gln Gly Val Tyr Phe Met
1               5                   10                  15

Ala Val Ala Leu Asp Arg Asn Arg Asn Leu Lys Arg Ile Asp Ile Pro
            20                  25                  30

Ser Lys Arg Phe Asp Gly Val Ser Thr Ser Phe Val Ala Cys Asn Gly
        35                  40                  45

Glu His Leu Gly Leu Pro Val Asn Leu Lys Lys Glu Phe Leu Ser Cys
    50                  55                  60

Ile Gln Arg Ala Ser Ser Ser Arg Ser Ser Asn Thr Ile Val Gln Phe
65                  70                  75                  80

Ala Asn Leu Pro Glu Gln Gly Lys Lys Val Val Glu Phe Asp Phe Asn
                85                  90                  95

Lys Tyr Met Leu Ser Lys Ala Met Ala Val Thr Glu Ala Leu Asp Lys
            100                 105                 110

Ala Ile Pro His Ser Tyr Pro Gln Lys Ile His Glu Ser Met Arg Tyr
        115                 120                 125

Ser Leu Leu Ala Gly Gly Lys Arg Val Arg Pro Val Leu Cys Ile Ala
    130                 135                 140

Ala Cys Glu Leu Val Gly Gly Arg Glu Glu Leu Ala Met Pro Thr Ala
145                 150                 155                 160

Cys Ala Met Glu Met Ile His Thr Met Ser Leu Ile His Asp Asp Leu
                165                 170                 175

Pro Cys Met Asp Asn Asp Asp Leu Arg Arg Gly Lys Pro Thr Asn His
            180                 185                 190

Lys Val Phe Gly Gln Asp Thr Ala Leu Leu Ala Gly Asp Ala Leu His
        195                 200                 205

Ala Phe Ala Phe Glu His Ile Val Ala Phe Thr Ser Lys Ser Val Gly
    210                 215                 220

Ser Asp Gly Ile Leu Arg Ala Val Thr Glu Leu Ala Arg Ala Thr Gly
```

```
                  225                 230                 235                 240

Pro Gln Gly Ile Met Gly Gly Gln Ile Val Asp Ile Ala Ser Glu Arg
                245                 250                 255

Asp Ala Phe Val Asp Leu Gln Thr Leu Glu Trp Ile His Ile His Lys
            260                 265                 270

Thr Ala Val Leu Phe Glu Cys Ala Thr Val Cys Gly Ala Ile Ile Gly
                275                 280                 285

Gly Ala Ser Gly Asp Glu Ile Glu Arg Ile Arg Arg Phe Ala Arg Tyr
        290                 295                 300

Leu Gly Leu Leu Phe Gln Val Val Asp Asp Ile Leu Asp Val Thr Lys
305                 310                 315                 320

Ser Ser Glu Asp Leu Gly Lys Thr Ala Gly Lys Asp Leu Val Ser Asp
                325                 330                 335

Lys Ala Thr Tyr Pro Lys Leu Met Gly Leu Glu Lys Ala Lys Gly Phe
                340                 345                 350

Ser Leu Glu Leu Leu Asn Lys Ala Lys Glu Glu Leu Ser Cys Phe Asp
            355                 360                 365

Pro Met Lys Ala Ala Pro Leu Phe Gly Leu Ala Asp Tyr Met Ala Leu
    370                 375                 380

Arg Gln Asn
385

<210> SEQ ID NO 8
<211> LENGTH: 891
<212> TYPE: DNA
<213> ORGANISM: Taxus Canadensis

<400> SEQUENCE: 8
gaatttgatt tcaacgagta tatgaagtcc aaggctgtgg cagtggatgc ggcactggat         60
aaggcaatcc cacttgaata tcctgaaaaa atacatgaat caatgaggta ttcacttcta        120
gcaggaggta agcgcgtcag gcctgctctg tgcattgcag catgtgagct tgtaggaggg        180
agtcaggacc ttgccatgcc aactgcctgt gcaatggaga tgattcatac catgtctctg        240
attcatgatg acttgccgtg catggataat gatgatttca gaagagggaa gccaacaaat        300
cacaaggtct ttggagagga cactgctgtt cttgcagggg acgccctgct tcatttgca         360 tttgagcata ttgctgtggc tacaagcaag actgtgccta gtgataggac tttaagggtg        420
atatctgaat tgggtaagac aataggctct caagggcttg tagggggca ggtggttgat         480 attacatccg aggggatgc taatgtggac ctgaaaaccc tggaatggat tcatatacac        540
aagactgctg tgctcttgga atgttcagtt gtgagtggag ggatccttgg tggtgctaca        600
gaggacgaga ttgcgagaat tcggcggtac gcccggtgtg tggggcttct gtttcaggtt        660
gtggatgaca tacttgatgt cactaaatct tctgaagaat tgggaaagac tgcaggaaag        720
gatttgctta ctgataaggc tacttatccc aagttgatgg gcctggagaa agcaaaagaa        780
tttgccgctg aattggcgac gagagccaag gaagagctgt catcctttga tcagataaag        840
gctgcacctt gttgggtctt gcagattac attgcattca ggcaaaactg a                891

<210> SEQ ID NO 9
<211> LENGTH: 891
<212> TYPE: DNA
<213> ORGANISM: Abies Grandis
<220> FEATURE:
<221> NAME/KEY: CDS
<222> LOCATION: (1)..(888)
```

<400> SEQUENCE: 9

```
atg ttt gat ttc aac aag tac atg gat tcc aag gca atg aca gtg aat      48
Met Phe Asp Phe Asn Lys Tyr Met Asp Ser Lys Ala Met Thr Val Asn
1               5                   10                  15 gag gcg ttg aat aag gct atc cca ctt cgt tat ccc cag aaa ata tat      96
Glu Ala Leu Asn Lys Ala Ile Pro Leu Arg Tyr Pro Gln Lys Ile Tyr
            20                  25                  30 gaa tcc atg agg tat tct ctt ctg gca gga ggg aaa cga gtt cgt cct     144
Glu Ser Met Arg Tyr Ser Leu Leu Ala Gly Gly Lys Arg Val Arg Pro
        35                  40                  45 gtt ctg tgc att gca gca tgt gag ctt gtt gga gga acc gag gag ctt     192
Val Leu Cys Ile Ala Ala Cys Glu Leu Val Gly Gly Thr Glu Glu Leu
    50                  55                  60 gcg att cca act gcc tgt gca atc gaa atg atc cac aca atg tct ttg     240
Ala Ile Pro Thr Ala Cys Ala Ile Glu Met Ile His Thr Met Ser Leu
65                  70                  75                  80 atg cat gat gac ttg cct tgc ata gac aat gat gat tta cgg cga ggg     288
Met His Asp Asp Leu Pro Cys Ile Asp Asn Asp Asp Leu Arg Arg Gly
                85                  90                  95 aaa cct aca aac cat aag atc ttc ggg gaa gat act gct gtt act gca     336
Lys Pro Thr Asn His Lys Ile Phe Gly Glu Asp Thr Ala Val Thr Ala
            100                 105                 110 ggg aat gcg ctt cat tct tac gcc ttt gag cat att gca gtt tcc aca     384
Gly Asn Ala Leu His Ser Tyr Ala Phe Glu His Ile Ala Val Ser Thr
        115                 120                 125 agc aaa act gtg ggg gct gat agg att ttg agg atg gta tct gaa ctg     432
Ser Lys Thr Val Gly Ala Asp Arg Ile Leu Arg Met Val Ser Glu Leu
    130                 135                 140 ggt aga gca aca ggc tct gaa ggg gtt atg ggt ggc cag atg gtc gat     480
Gly Arg Ala Thr Gly Ser Glu Gly Val Met Gly Gly Gln Met Val Asp
145                 150                 155                 160 att gcc agc gaa ggg gat cct tct att gac ctt cag act ctg gaa tgg     528
Ile Ala Ser Glu Gly Asp Pro Ser Ile Asp Leu Gln Thr Leu Glu Trp
                165                 170                 175 att cat att cac aag act gca atg ctc ttg gag tgc tcg gtt gtg tgt     576
Ile His Ile His Lys Thr Ala Met Leu Leu Glu Cys Ser Val Val Cys
            180                 185                 190 ggg gcg atc atc ggt ggt gct tcg gag att gtg atc gag aga gct cga     624
Gly Ala Ile Ile Gly Gly Ala Ser Glu Ile Val Ile Glu Arg Ala Arg
        195                 200                 205 agg tat gcc cgt tgc gtg ggg ctt ctt ttt cag gtt gtg gat gac ata     672
Arg Tyr Ala Arg Cys Val Gly Leu Leu Phe Gln Val Val Asp Asp Ile
    210                 215                 220 ctc gat gtc acg aaa tca tca gac gaa ctg ggc aag act gca gga aag     720
Leu Asp Val Thr Lys Ser Ser Asp Glu Leu Gly Lys Thr Ala Gly Lys
225                 230                 235                 240 gat ttg att agt gat aag gca act tat cca aag ctc atg ggt ttg gag     768
Asp Leu Ile Ser Asp Lys Ala Thr Tyr Pro Lys Leu Met Gly Leu Glu
                245                 250                 255 aaa gca aag gag ttt tct gat gaa ttg ttg aac aga gct aag gga gag     816
Lys Ala Lys Glu Phe Ser Asp Glu Leu Leu Asn Arg Ala Lys Gly Glu
            260                 265                 270 tta tct tgc ttc gat cca gtg aag gca gca cct ctg ttg ggt ctt gca     864
Leu Ser Cys Phe Asp Pro Val Lys Ala Ala Pro Leu Leu Gly Leu Ala
        275                 280                 285 gat tac gtg gca ttc aga caa aat tga                                 891
Asp Tyr Val Ala Phe Arg Gln Asn
    290                 295
```

<210> SEQ ID NO 10
<211> LENGTH: 296
<212> TYPE: PRT
<213> ORGANISM: Abies Grandis

<400> SEQUENCE: 10

Met Phe Asp Phe Asn Lys Tyr Met Asp Ser Lys Ala Met Thr Val Asn
1               5                   10                  15

Glu Ala Leu Asn Lys Ala Ile Pro Leu Arg Tyr Pro Gln Lys Ile Tyr
            20                  25                  30

Glu Ser Met Arg Tyr Ser Leu Leu Ala Gly Gly Lys Arg Val Arg Pro
        35                  40                  45

Val Leu Cys Ile Ala Ala Cys Glu Leu Val Gly Gly Thr Glu Glu Leu
50                  55                  60

Ala Ile Pro Thr Ala Cys Ala Ile Glu Met Ile His Thr Met Ser Leu
65                  70                  75                  80

Met His Asp Asp Leu Pro Cys Ile Asp Asn Asp Asp Leu Arg Arg Gly
                85                  90                  95

Lys Pro Thr Asn His Lys Ile Phe Gly Glu Asp Thr Ala Val Thr Ala
            100                 105                 110

Gly Asn Ala Leu His Ser Tyr Ala Phe Glu His Ile Ala Val Ser Thr
        115                 120                 125

Ser Lys Thr Val Gly Ala Asp Arg Ile Leu Arg Met Val Ser Glu Leu
    130                 135                 140

Gly Arg Ala Thr Gly Ser Glu Gly Val Met Gly Gly Gln Met Val Asp
145                 150                 155                 160

Ile Ala Ser Glu Gly Asp Pro Ser Ile Asp Leu Gln Thr Leu Glu Trp
                165                 170                 175

Ile His Ile His Lys Thr Ala Met Leu Leu Glu Cys Ser Val Val Cys
            180                 185                 190

Gly Ala Ile Ile Gly Gly Ala Ser Glu Ile Val Ile Glu Arg Ala Arg
        195                 200                 205

Arg Tyr Ala Arg Cys Val Gly Leu Leu Phe Gln Val Val Asp Asp Ile
    210                 215                 220

Leu Asp Val Thr Lys Ser Ser Asp Glu Leu Gly Lys Thr Ala Gly Lys
225                 230                 235                 240

Asp Leu Ile Ser Asp Lys Ala Thr Tyr Pro Lys Leu Met Gly Leu Glu
                245                 250                 255

Lys Ala Lys Glu Phe Ser Asp Glu Leu Leu Asn Arg Ala Lys Gly Glu
            260                 265                 270

Leu Ser Cys Phe Asp Pro Val Lys Ala Ala Pro Leu Leu Gly Leu Ala
        275                 280                 285

Asp Tyr Val Ala Phe Arg Gln Asn
    290                 295

<210> SEQ ID NO 11
<211> LENGTH: 915
<212> TYPE: DNA
<213> ORGANISM: Abies Grandis
<220> FEATURE:
<221> NAME/KEY: CDS
<222> LOCATION: (1)..(912)

<400> SEQUENCE: 11 atg ttt gat ttc aac aag tac atg gat tcc aag gca atg aca gtg aat        48
Met Phe Asp Phe Asn Lys Tyr Met Asp Ser Lys Ala Met Thr Val Asn
1               5                   10                  15

```
gag gcg ttg aat aag gct atc cca ctt cgt tat ccc cag aaa ata tat       96
Glu Ala Leu Asn Lys Ala Ile Pro Leu Arg Tyr Pro Gln Lys Ile Tyr
             20                  25                  30 gaa tcc atg agg tat tct ctt ctg gca gga ggg aaa cga gtt cgt cct      144
Glu Ser Met Arg Tyr Ser Leu Leu Ala Gly Gly Lys Arg Val Arg Pro
         35                  40                  45 gtt ctg tgc att gca gca tgt gag ctt gtt gga gga acc gag gag ctt      192
Val Leu Cys Ile Ala Ala Cys Glu Leu Val Gly Gly Thr Glu Glu Leu
     50                  55                  60 gcg att cca act gcc tgt gca atc gaa atg atc cac aca atg tct ttg      240
Ala Ile Pro Thr Ala Cys Ala Ile Glu Met Ile His Thr Met Ser Leu
 65                  70                  75                  80 atg cat gat gac ttg cct tgc ata gac aat gat gat tta cgg cga ggg      288
Met His Asp Asp Leu Pro Cys Ile Asp Asn Asp Asp Leu Arg Arg Gly
                 85                  90                  95 aaa cct aca aac cat aag atc ttc ggg gaa gat act gct gtt act gca      336
Lys Pro Thr Asn His Lys Ile Phe Gly Glu Asp Thr Ala Val Thr Ala
            100                 105                 110 ggg aat gcg ctt cat tct tac gcc ttt gag cat att gca gtt tcc aca      384
Gly Asn Ala Leu His Ser Tyr Ala Phe Glu His Ile Ala Val Ser Thr
        115                 120                 125 agc aaa act gtg ggg gct gat agg att ttg agg atg gta tct gaa ctg      432
Ser Lys Thr Val Gly Ala Asp Arg Ile Leu Arg Met Val Ser Glu Leu
    130                 135                 140 ggt aga gca aca ggc tct gaa ggg gtt atg ggt ggc cag atg gtc gat      480
Gly Arg Ala Thr Gly Ser Glu Gly Val Met Gly Gly Gln Met Val Asp
145                 150                 155                 160 att gcc agc gaa ggg gat cct tct att gac ctt cag act ctg gaa tgg      528
Ile Ala Ser Glu Gly Asp Pro Ser Ile Asp Leu Gln Thr Leu Glu Trp
                165                 170                 175 att cat att cac aag act gca atg ctc ttg gag tgc tcg gtt gtg tgt      576
Ile His Ile His Lys Thr Ala Met Leu Leu Glu Cys Ser Val Val Cys
            180                 185                 190 ggg gcg atc atc ggt ggt gct tcg gag att gtg atc gag aga gct cga      624
Gly Ala Ile Ile Gly Gly Ala Ser Glu Ile Val Ile Glu Arg Ala Arg
        195                 200                 205 agg tat gcc cgt tgc gtg ggg ctt ctt ttt cag gtt gtg gat gac ata      672
Arg Tyr Ala Arg Cys Val Gly Leu Leu Phe Gln Val Val Asp Asp Ile
    210                 215                 220 ctc gat gtc acg aaa tca tca gac gaa ctg ggc aag act gca gga aag      720
Leu Asp Val Thr Lys Ser Ser Asp Glu Leu Gly Lys Thr Ala Gly Lys
225                 230                 235                 240 gat ttg att agt gat aag gca act tat cca aag ctc atg ggt ttg gag      768
Asp Leu Ile Ser Asp Lys Ala Thr Tyr Pro Lys Leu Met Gly Leu Glu
                245                 250                 255 aaa gca aag gag ttt tct gat gaa ttg ttg aac aga gct aag gga gag      816
Lys Ala Lys Glu Phe Ser Asp Glu Leu Leu Asn Arg Ala Lys Gly Glu
            260                 265                 270 tta tct tgc ttc gat cca gtg aag gca gca cct ctg ttg ggt ctt gca      864
Leu Ser Cys Phe Asp Pro Val Lys Ala Ala Pro Leu Leu Gly Leu Ala
        275                 280                 285 gat tac gtg gca ttc aga caa aat ctc gag cac cac cac cac cac cac      912
Asp Tyr Val Ala Phe Arg Gln Asn Leu Glu His His His His His His
    290                 295                 300 tga                                                                   915
```

<210> SEQ ID NO 12
<211> LENGTH: 304
<212> TYPE: PRT
<213> ORGANISM: Abies Grandis

<400> SEQUENCE: 12

```
Met Phe Asp Phe Asn Lys Tyr Met Asp Ser Lys Ala Met Thr Val Asn
1               5                   10                  15
Glu Ala Leu Asn Lys Ala Ile Pro Leu Arg Tyr Pro Gln Lys Ile Tyr
            20                  25                  30
Glu Ser Met Arg Tyr Ser Leu Leu Ala Gly Gly Lys Arg Val Arg Pro
        35                  40                  45
Val Leu Cys Ile Ala Ala Cys Glu Leu Val Gly Gly Thr Glu Glu Leu
50                  55                  60
Ala Ile Pro Thr Ala Cys Ala Ile Glu Met Ile His Thr Met Ser Leu
65                  70                  75                  80
Met His Asp Asp Leu Pro Cys Ile Asp Asn Asp Asp Leu Arg Arg Gly
                85                  90                  95
Lys Pro Thr Asn His Lys Ile Phe Gly Glu Asp Thr Ala Val Thr Ala
            100                 105                 110
Gly Asn Ala Leu His Ser Tyr Ala Phe Glu His Ile Ala Val Ser Thr
        115                 120                 125
Ser Lys Thr Val Gly Ala Asp Arg Ile Leu Arg Met Val Ser Glu Leu
130                 135                 140
Gly Arg Ala Thr Gly Ser Glu Gly Val Met Gly Gly Gln Met Val Asp
145                 150                 155                 160
Ile Ala Ser Glu Gly Asp Pro Ser Ile Asp Leu Gln Thr Leu Glu Trp
                165                 170                 175
Ile His Ile His Lys Thr Ala Met Leu Leu Glu Cys Ser Val Val Cys
            180                 185                 190
Gly Ala Ile Ile Gly Gly Ala Ser Glu Ile Val Ile Glu Arg Ala Arg
        195                 200                 205
Arg Tyr Ala Arg Cys Val Gly Leu Leu Phe Gln Val Val Asp Asp Ile
210                 215                 220
Leu Asp Val Thr Lys Ser Ser Asp Glu Leu Gly Lys Thr Ala Gly Lys
225                 230                 235                 240
Asp Leu Ile Ser Asp Lys Ala Thr Tyr Pro Lys Leu Met Gly Leu Glu
                245                 250                 255
Lys Ala Lys Glu Phe Ser Asp Glu Leu Leu Asn Arg Ala Lys Gly Glu
            260                 265                 270
Leu Ser Cys Phe Asp Pro Val Lys Ala Ala Pro Leu Leu Gly Leu Ala
        275                 280                 285
Asp Tyr Val Ala Phe Arg Gln Asn Leu Glu His His His His His His
290                 295                 300
```

<210> SEQ ID NO 13
<211> LENGTH: 891
<212> TYPE: DNA
<213> ORGANISM: Abies Grandis
<220> FEATURE:
<221> NAME/KEY: CDS
<222> LOCATION: (1)..(888)

<400> SEQUENCE: 13

```
atg ttt gat ttc aag gag tac ttg cat tcc aaa gca ata tca gtg aat     48
Met Phe Asp Phe Lys Glu Tyr Leu His Ser Lys Ala Ile Ser Val Asn
1               5                   10                  15 gag gca ctg gag agg gct gtc cca ctt cgc tat cct gaa aaa ata cat     96
Glu Ala Leu Glu Arg Ala Val Pro Leu Arg Tyr Pro Glu Lys Ile His
            20                  25                  30
```

```
gaa gct atg agg tat tct ctt cta gca gga ggg aag cgg att cgt cct      144
Glu Ala Met Arg Tyr Ser Leu Leu Ala Gly Gly Lys Arg Ile Arg Pro
        35                  40                  45 att ctg act att gca gca tgt gag ctt gtg gga ggg agt gag gag ctc      192
Ile Leu Thr Ile Ala Ala Cys Glu Leu Val Gly Gly Ser Glu Glu Leu
 50                  55                  60 gcc atg cca act gcc tgt gca atg gag atg atc cac aca atg tct ttg      240
Ala Met Pro Thr Ala Cys Ala Met Glu Met Ile His Thr Met Ser Leu
 65                  70                  75                  80 att cat gat gat ttg cct tcc atg gac aat gat gat tta cgc cga ggt      288
Ile His Asp Asp Leu Pro Ser Met Asp Asn Asp Asp Leu Arg Arg Gly
             85                  90                  95 aag ctt aca aac cac aag gtc ttt ggc gaa ggc act gct gtt ctt gca      336
Lys Leu Thr Asn His Lys Val Phe Gly Glu Gly Thr Ala Val Leu Ala
            100                 105                 110 ggg gat gca ctt ctt tca ttt gca ttt gag cac att gca gtg tcc aca      384
Gly Asp Ala Leu Leu Ser Phe Ala Phe Glu His Ile Ala Val Ser Thr
        115                 120                 125 agg aaa act gtg gcg agt cat agg gtt ttg agg gtg gta tct gaa ttg      432
Arg Lys Thr Val Ala Ser His Arg Val Leu Arg Val Val Ser Glu Leu
    130                 135                 140 ggt aag gca ata ggc tct caa ggg gtt gct ggt ggg cag gtt gct gat      480
Gly Lys Ala Ile Gly Ser Gln Gly Val Ala Gly Gly Gln Val Ala Asp
145                 150                 155                 160 att acc agt gaa ggg gat cca tct gtt ggg ctt gag act ctc gaa tgg      528
Ile Thr Ser Glu Gly Asp Pro Ser Val Gly Leu Glu Thr Leu Glu Trp
                165                 170                 175 att cac att cac aag act gca gtg ctc ttg gag tgc gcc gtt gtg agt      576
Ile His Ile His Lys Thr Ala Val Leu Leu Glu Cys Ala Val Val Ser
            180                 185                 190 ggg gcg atc atc ggt ggc gct tca gag aat gaa att gag aga act gga      624
Gly Ala Ile Ile Gly Gly Ala Ser Glu Asn Glu Ile Glu Arg Thr Gly
        195                 200                 205 agg tat gcc cgt tgc gtt ggg ctt ctg ttt cag gtt gtg gat gac ata      672
Arg Tyr Ala Arg Cys Val Gly Leu Leu Phe Gln Val Val Asp Asp Ile
    210                 215                 220 ctc gat gtc acc aga tca tca gaa gaa ttg gga aag act gca gga aag      720
Leu Asp Val Thr Arg Ser Ser Glu Glu Leu Gly Lys Thr Ala Gly Lys
225                 230                 235                 240 gat ttg gtt agt gat aag gcc act tat ccc aag ctg atg ggt ttg gag      768
Asp Leu Val Ser Asp Lys Ala Thr Tyr Pro Lys Leu Met Gly Leu Glu
                245                 250                 255 aaa gcg aag gaa ttt gct gat gaa ttg ttg gac aga gct aag gag gag      816
Lys Ala Lys Glu Phe Ala Asp Glu Leu Leu Asp Arg Ala Lys Glu Glu
            260                 265                 270 tta tct tgc ttc aac cca gct aag gct gca cct ctg ttg ggt ctt gca      864
Leu Ser Cys Phe Asn Pro Ala Lys Ala Ala Pro Leu Leu Gly Leu Ala
        275                 280                 285 gat tac att gca tta aga cag aac tga                                  891
Asp Tyr Ile Ala Leu Arg Gln Asn
    290                 295

<210> SEQ ID NO 14
<211> LENGTH: 296
<212> TYPE: PRT
<213> ORGANISM: Abies Grandis

<400> SEQUENCE: 14

Met Phe Asp Phe Lys Glu Tyr Leu His Ser Lys Ala Ile Ser Val Asn
1               5                   10                  15
```

```
Glu Ala Leu Glu Arg Ala Val Pro Leu Arg Tyr Pro Glu Lys Ile His
             20                  25                  30

Glu Ala Met Arg Tyr Ser Leu Leu Ala Gly Gly Lys Arg Ile Arg Pro
         35                  40                  45

Ile Leu Thr Ile Ala Ala Cys Glu Leu Val Gly Gly Ser Glu Glu Leu
     50                  55                  60

Ala Met Pro Thr Ala Cys Ala Met Glu Met Ile His Thr Met Ser Leu
 65                  70                  75                  80

Ile His Asp Asp Leu Pro Ser Met Asp Asn Asp Leu Arg Arg Gly
                 85                  90                  95

Lys Leu Thr Asn His Lys Val Phe Gly Glu Gly Thr Ala Val Leu Ala
             100                 105                 110

Gly Asp Ala Leu Leu Ser Phe Ala Phe Glu His Ile Ala Val Ser Thr
         115                 120                 125

Arg Lys Thr Val Ala Ser His Arg Val Leu Arg Val Val Ser Glu Leu
    130                 135                 140

Gly Lys Ala Ile Gly Ser Gln Gly Val Ala Gly Gly Gln Val Ala Asp
145                 150                 155                 160

Ile Thr Ser Glu Gly Asp Pro Ser Val Gly Leu Glu Thr Leu Glu Trp
                165                 170                 175

Ile His Ile His Lys Thr Ala Val Leu Leu Glu Cys Ala Val Val Ser
            180                 185                 190

Gly Ala Ile Ile Gly Gly Ala Ser Glu Asn Glu Ile Glu Arg Thr Gly
        195                 200                 205

Arg Tyr Ala Arg Cys Val Gly Leu Leu Phe Gln Val Val Asp Asp Ile
    210                 215                 220

Leu Asp Val Thr Arg Ser Ser Glu Glu Leu Gly Lys Thr Ala Gly Lys
225                 230                 235                 240

Asp Leu Val Ser Asp Lys Ala Thr Tyr Pro Lys Leu Met Gly Leu Glu
                245                 250                 255

Lys Ala Lys Glu Phe Ala Asp Glu Leu Leu Asp Arg Ala Lys Glu Glu
            260                 265                 270

Leu Ser Cys Phe Asn Pro Ala Lys Ala Ala Pro Leu Leu Gly Leu Ala
        275                 280                 285

Asp Tyr Ile Ala Leu Arg Gln Asn
    290                 295

<210> SEQ ID NO 15
<211> LENGTH: 915
<212> TYPE: DNA
<213> ORGANISM: Abies Grandis
<220> FEATURE:
<221> NAME/KEY: CDS
<222> LOCATION: (1)..(912)

<400> SEQUENCE: 15 atg ttt gat ttc aag gag tac ttg cat tcc aaa gca ata tca gtg aat     48
Met Phe Asp Phe Lys Glu Tyr Leu His Ser Lys Ala Ile Ser Val Asn
 1               5                  10                  15 gag gca ctg gag agg gct gtc cca ctt cgc tat cct gaa aaa ata cat     96
Glu Ala Leu Glu Arg Ala Val Pro Leu Arg Tyr Pro Glu Lys Ile His
             20                  25                  30 gaa gct atg agg tat tct ctt cta gca gga ggg aag cgg att cgt cct    144
Glu Ala Met Arg Tyr Ser Leu Leu Ala Gly Gly Lys Arg Ile Arg Pro
         35                  40                  45 att ctg act att gca gca tgt gag ctt gtg gga ggg agt gag gag ctc    192
Ile Leu Thr Ile Ala Ala Cys Glu Leu Val Gly Gly Ser Glu Glu Leu
```

```
                50                  55                  60
gcc atg cca act gcc tgt gca atg gag atg atc cac aca atg tct ttg      240
Ala Met Pro Thr Ala Cys Ala Met Glu Met Ile His Thr Met Ser Leu
 65              70                  75                  80 att cat gat gat ttg cct tcc atg gac aat gat gat tta cgc cga ggt      288
Ile His Asp Asp Leu Pro Ser Met Asp Asn Asp Asp Leu Arg Arg Gly
             85                  90                  95 aag ctt aca aac cac aag gtc ttt ggc gaa ggc act gct gtt ctt gca      336
Lys Leu Thr Asn His Lys Val Phe Gly Glu Gly Thr Ala Val Leu Ala
        100                 105                 110 ggg gat gca ctt ctt tca ttt gca ttt gag cac att gca gtg tcc aca      384
Gly Asp Ala Leu Leu Ser Phe Ala Phe Glu His Ile Ala Val Ser Thr
        115                 120                 125 agg aaa act gtg gcg agt cat agg gtt ttg agg gtg gta tct gaa ttg      432
Arg Lys Thr Val Ala Ser His Arg Val Leu Arg Val Val Ser Glu Leu
        130                 135                 140 ggt aag gca ata ggc tct caa ggg gtt gct ggt ggg cag gtt gct gat      480
Gly Lys Ala Ile Gly Ser Gln Gly Val Ala Gly Gly Gln Val Ala Asp
145                 150                 155                 160 att acc agt gaa ggg gat cca tct gtt ggg ctt gag act ctc gaa tgg      528
Ile Thr Ser Glu Gly Asp Pro Ser Val Gly Leu Glu Thr Leu Glu Trp
                165                 170                 175 att cac att cac aag act gca gtg ctc ttg gag tgc gcc gtt gtg agt      576
Ile His Ile His Lys Thr Ala Val Leu Leu Glu Cys Ala Val Val Ser
            180                 185                 190 ggg gcg atc atc ggt ggc gct tca gag aat gaa att gag aga act gga      624
Gly Ala Ile Ile Gly Gly Ala Ser Glu Asn Glu Ile Glu Arg Thr Gly
        195                 200                 205 agg tat gcc cgt tgc gtt ggg ctt ctg ttt cag gtt gtg gat gac ata      672
Arg Tyr Ala Arg Cys Val Gly Leu Leu Phe Gln Val Val Asp Asp Ile
    210                 215                 220 ctc gat gtc acc aga tca tca gaa gaa ttg gga aag act gca gga aag      720
Leu Asp Val Thr Arg Ser Ser Glu Glu Leu Gly Lys Thr Ala Gly Lys
225                 230                 235                 240 gat ttg gtt agt gat aag gcc act tat ccc aag ctg atg ggt ttg gag      768
Asp Leu Val Ser Asp Lys Ala Thr Tyr Pro Lys Leu Met Gly Leu Glu
                245                 250                 255 aaa gcg aag gaa ttt gct gat gaa ttg ttg gac aga gct aag gag gag      816
Lys Ala Lys Glu Phe Ala Asp Glu Leu Leu Asp Arg Ala Lys Glu Glu
            260                 265                 270 tta tct tgc ttc aac cca gct aag gct gca cct ctg ttg ggt ctt gca      864
Leu Ser Cys Phe Asn Pro Ala Lys Ala Ala Pro Leu Leu Gly Leu Ala
        275                 280                 285 gat tac att gca tta aga cag aac ctc gag cac cac cac cac cac cac      912
Asp Tyr Ile Ala Leu Arg Gln Asn Leu Glu His His His His His His
    290                 295                 300 tga                                                                   915

<210> SEQ ID NO 16
<211> LENGTH: 304
<212> TYPE: PRT
<213> ORGANISM: Abies Grandis

<400> SEQUENCE: 16

Met Phe Asp Phe Lys Glu Tyr Leu His Ser Lys Ala Ile Ser Val Asn
 1               5                  10                  15

Glu Ala Leu Glu Arg Ala Val Pro Leu Arg Tyr Pro Glu Lys Ile His
            20                  25                  30

Glu Ala Met Arg Tyr Ser Leu Leu Ala Gly Gly Lys Arg Ile Arg Pro
```

-continued

```
                35                  40                  45
Ile Leu Thr Ile Ala Ala Cys Glu Leu Val Gly Gly Ser Glu Glu Leu
 50                  55                  60

Ala Met Pro Thr Ala Cys Ala Met Glu Met Ile His Thr Met Ser Leu
 65                  70                  75                  80

Ile His Asp Asp Leu Pro Ser Met Asp Asn Asp Leu Arg Arg Gly
                 85                  90                  95

Lys Leu Thr Asn His Lys Val Phe Gly Glu Gly Thr Ala Val Leu Ala
                100                 105                 110

Gly Asp Ala Leu Leu Ser Phe Ala Phe Glu His Ile Ala Val Ser Thr
            115                 120                 125

Arg Lys Thr Val Ala Ser His Arg Val Leu Arg Val Val Ser Glu Leu
    130                 135                 140

Gly Lys Ala Ile Gly Ser Gln Gly Val Ala Gly Gln Val Ala Asp
145                 150                 155                 160

Ile Thr Ser Glu Gly Asp Pro Ser Val Gly Leu Glu Thr Leu Glu Trp
                165                 170                 175

Ile His Ile His Lys Thr Ala Val Leu Leu Glu Cys Ala Val Val Ser
            180                 185                 190

Gly Ala Ile Ile Gly Gly Ala Ser Glu Asn Glu Ile Glu Arg Thr Gly
        195                 200                 205

Arg Tyr Ala Arg Cys Val Gly Leu Leu Phe Gln Val Val Asp Asp Ile
    210                 215                 220

Leu Asp Val Thr Arg Ser Ser Glu Glu Leu Gly Lys Thr Ala Gly Lys
225                 230                 235                 240

Asp Leu Val Ser Asp Lys Ala Thr Tyr Pro Lys Leu Met Gly Leu Glu
                245                 250                 255

Lys Ala Lys Glu Phe Ala Asp Glu Leu Leu Asp Arg Ala Lys Glu Glu
            260                 265                 270

Leu Ser Cys Phe Asn Pro Ala Lys Ala Ala Pro Leu Leu Gly Leu Ala
        275                 280                 285

Asp Tyr Ile Ala Leu Arg Gln Asn Leu Glu His His His His His His
    290                 295                 300
```

<210> SEQ ID NO 17
<211> LENGTH: 891
<212> TYPE: DNA
<213> ORGANISM: Abies Grandis
<220> FEATURE:
<221> NAME/KEY: CDS
<222> LOCATION: (1)..(888)

<400> SEQUENCE: 17

```
atg ttt gat ttc aat aag tac atg ctt tcc aag gca atg gca gtg act       48
Met Phe Asp Phe Asn Lys Tyr Met Leu Ser Lys Ala Met Ala Val Thr
 1               5                  10                  15 gag gca ttg gat aag gct atc cca cat agt tat ccc cag aaa ata cat       96
Glu Ala Leu Asp Lys Ala Ile Pro His Ser Tyr Pro Gln Lys Ile His
                 20                  25                  30 gaa tcc atg agg tat tct ctt ctg gca ggg ggg aag cgc gtt cgt cct      144
Glu Ser Met Arg Tyr Ser Leu Leu Ala Gly Gly Lys Arg Val Arg Pro
        35                  40                  45 gtt ctg tgc att gct gcg tgt gaa ctt gtg gga gga agg gag gag ctc      192
Val Leu Cys Ile Ala Ala Cys Glu Leu Val Gly Gly Arg Glu Glu Leu
 50                  55                  60 gcc atg cca act gcc tgc gca atg gaa atg atc cac aca atg tct ttg      240
Ala Met Pro Thr Ala Cys Ala Met Glu Met Ile His Thr Met Ser Leu
```

```
att cat gat gac tta cct tgc atg gac aac gat gat tta cgg cga ggt    288
Ile His Asp Asp Leu Pro Cys Met Asp Asn Asp Asp Leu Arg Arg Gly
             85                  90                  95 aag cct aca aac cat aag gtc ttc ggc cag gac act gct ctt ctt gca    336
Lys Pro Thr Asn His Lys Val Phe Gly Gln Asp Thr Ala Leu Leu Ala
            100                 105                 110 ggg gat gca ctt cat gca ttt gcc ttt gag cac att gta gcc ttt aca    384
Gly Asp Ala Leu His Ala Phe Ala Phe Glu His Ile Val Ala Phe Thr
        115                 120                 125 agc aaa tct gtg ggg agt gat ggg att ttg agg gcg gtt act gaa ttg    432
Ser Lys Ser Val Gly Ser Asp Gly Ile Leu Arg Ala Val Thr Glu Leu
    130                 135                 140 gct aga gca aca ggc cct caa ggg att atg ggt ggc cag att gtc gat    480
Ala Arg Ala Thr Gly Pro Gln Gly Ile Met Gly Gly Gln Ile Val Asp
145                 150                 155                 160 att gcg agc gag cgg gat gct ttt gtt gac ctt cag act ctg gaa tgg    528
Ile Ala Ser Glu Arg Asp Ala Phe Val Asp Leu Gln Thr Leu Glu Trp
                165                 170                 175 atc cat att cac aag act gcg gtg ctc ttc gag tgc gcg act gtg tgt    576
Ile His Ile His Lys Thr Ala Val Leu Phe Glu Cys Ala Thr Val Cys
            180                 185                 190 ggg gcg atc atc gga ggt gct tcg ggg gat gaa att gag aga att cga    624
Gly Ala Ile Ile Gly Gly Ala Ser Gly Asp Glu Ile Glu Arg Ile Arg
        195                 200                 205 agg ttt gcc cgt tat ttg ggg ctt ctg ttt caa gtc gtg gat gac ata    672
Arg Phe Ala Arg Tyr Leu Gly Leu Leu Phe Gln Val Val Asp Asp Ile
    210                 215                 220 ctc gat gtc aca aaa tct tct gaa gat ttg ggt aag act gca gga aag    720
Leu Asp Val Thr Lys Ser Ser Glu Asp Leu Gly Lys Thr Ala Gly Lys
225                 230                 235                 240 gat ttg gtt agt gat aag gcc act tat ccc aag ctg atg ggt tta gag    768
Asp Leu Val Ser Asp Lys Ala Thr Tyr Pro Lys Leu Met Gly Leu Glu
                245                 250                 255 aaa gca aag gga ttt tct ctt gaa ttg ttg aac aaa gct aag gag gag    816
Lys Ala Lys Gly Phe Ser Leu Glu Leu Leu Asn Lys Ala Lys Glu Glu
            260                 265                 270 tta tca tgc ttc gat cca atg aag gct gca cct ctg ttc ggt ctt gca    864
Leu Ser Cys Phe Asp Pro Met Lys Ala Ala Pro Leu Phe Gly Leu Ala
        275                 280                 285 gat tac atg gca ctc aga cag aat tga                                891
Asp Tyr Met Ala Leu Arg Gln Asn
    290                 295

<210> SEQ ID NO 18
<211> LENGTH: 296
<212> TYPE: PRT
<213> ORGANISM: Abies Grandis

<400> SEQUENCE: 18

Met Phe Asp Phe Asn Lys Tyr Met Leu Ser Lys Ala Met Ala Val Thr
1               5                   10                  15

Glu Ala Leu Asp Lys Ala Ile Pro His Ser Tyr Pro Gln Lys Ile His
            20                  25                  30

Glu Ser Met Arg Tyr Ser Leu Leu Ala Gly Gly Lys Arg Val Arg Pro
        35                  40                  45

Val Leu Cys Ile Ala Ala Cys Glu Leu Val Gly Gly Arg Glu Glu Leu
    50                  55                  60

Ala Met Pro Thr Ala Cys Ala Met Glu Met Ile His Thr Met Ser Leu
```

```
             65                  70                  75                  80
Ile His Asp Asp Leu Pro Cys Met Asp Asn Asp Asp Leu Arg Arg Gly
                    85                  90                  95

Lys Pro Thr Asn His Lys Val Phe Gly Gln Asp Thr Ala Leu Leu Ala
                100                 105                 110

Gly Asp Ala Leu His Ala Phe Ala Phe Glu His Ile Val Ala Phe Thr
                115                 120                 125

Ser Lys Ser Val Gly Ser Asp Gly Ile Leu Arg Ala Val Thr Glu Leu
    130                 135                 140

Ala Arg Ala Thr Gly Pro Gln Gly Ile Met Gly Gly Gln Ile Val Asp
145                 150                 155                 160

Ile Ala Ser Glu Arg Asp Ala Phe Val Asp Leu Gln Thr Leu Glu Trp
                165                 170                 175

Ile His Ile His Lys Thr Ala Val Leu Phe Glu Cys Ala Thr Val Cys
                180                 185                 190

Gly Ala Ile Ile Gly Gly Ala Ser Gly Asp Glu Ile Glu Arg Ile Arg
            195                 200                 205

Arg Phe Ala Arg Tyr Leu Gly Leu Leu Phe Gln Val Val Asp Asp Ile
    210                 215                 220

Leu Asp Val Thr Lys Ser Ser Glu Asp Leu Gly Lys Thr Ala Gly Lys
225                 230                 235                 240

Asp Leu Val Ser Asp Lys Ala Thr Tyr Pro Lys Leu Met Gly Leu Glu
                245                 250                 255

Lys Ala Lys Gly Phe Ser Leu Glu Leu Leu Asn Lys Ala Lys Glu Glu
            260                 265                 270

Leu Ser Cys Phe Asp Pro Met Lys Ala Ala Pro Leu Phe Gly Leu Ala
        275                 280                 285

Asp Tyr Met Ala Leu Arg Gln Asn
    290                 295

<210> SEQ ID NO 19
<211> LENGTH: 915
<212> TYPE: DNA
<213> ORGANISM: Abies Grandis
<220> FEATURE:
<221> NAME/KEY: CDS
<222> LOCATION: (1)..(912)

<400> SEQUENCE: 19 atg ttt gat ttc aat aag tac atg ctt tcc aag gca atg gca gtg act         48
Met Phe Asp Phe Asn Lys Tyr Met Leu Ser Lys Ala Met Ala Val Thr
1               5                  10                  15 gag gca ttg gat aag gct atc cca cat agt tat ccc cag aaa ata cat         96
Glu Ala Leu Asp Lys Ala Ile Pro His Ser Tyr Pro Gln Lys Ile His
                20                  25                  30 gaa tcc atg agg tat tct ctt ctg gca ggg ggg aag cgc gtt cgt cct        144
Glu Ser Met Arg Tyr Ser Leu Leu Ala Gly Gly Lys Arg Val Arg Pro
            35                  40                  45 gtt ctg tgc att gct gcg tgt gaa ctt gtg gga gga agg gag gag ctc        192
Val Leu Cys Ile Ala Ala Cys Glu Leu Val Gly Gly Arg Glu Glu Leu
        50                  55                  60 gcc atg cca act gcc tgc gca atg gaa atg atc cac aca atg tct ttg        240
Ala Met Pro Thr Ala Cys Ala Met Glu Met Ile His Thr Met Ser Leu
65                  70                  75                  80 att cat gat gac tta cct tgc atg gac aac gat gat tta cgg cga ggt        288
Ile His Asp Asp Leu Pro Cys Met Asp Asn Asp Asp Leu Arg Arg Gly
                85                  90                  95
```

```
aag cct aca aac cat aag gtc ttc ggc cag gac act gct ctt ctt gca       336
Lys Pro Thr Asn His Lys Val Phe Gly Gln Asp Thr Ala Leu Leu Ala
            100                 105                 110 ggg gat gca ctt cat gca ttt gcc ttt gag cac att gta gcc ttt aca       384
Gly Asp Ala Leu His Ala Phe Ala Phe Glu His Ile Val Ala Phe Thr
        115                 120                 125 agc aaa tct gtg ggg agt gat ggg att ttg agg gcg gtt act gaa ttg       432
Ser Lys Ser Val Gly Ser Asp Gly Ile Leu Arg Ala Val Thr Glu Leu
    130                 135                 140 gct aga gca aca ggc cct caa ggg att atg ggt ggc cag att gtc gat       480
Ala Arg Ala Thr Gly Pro Gln Gly Ile Met Gly Gly Gln Ile Val Asp
145                 150                 155                 160 att gcg agc gag cgg gat gct ttt gtt gac ctt cag act ctg gaa tgg       528
Ile Ala Ser Glu Arg Asp Ala Phe Val Asp Leu Gln Thr Leu Glu Trp
                165                 170                 175 atc cat att cac aag act gcg gtg ctc ttc gag tgc gcg act gtg tgt       576
Ile His Ile His Lys Thr Ala Val Leu Phe Glu Cys Ala Thr Val Cys
            180                 185                 190 ggg gcg atc atc gga ggt gct tcg ggg gat gaa att gag aga att cga       624
Gly Ala Ile Ile Gly Gly Ala Ser Gly Asp Glu Ile Glu Arg Ile Arg
        195                 200                 205 agg ttt gcc cgt tat ttg ggg ctt ctg ttt caa gtc gtg gat gac ata       672
Arg Phe Ala Arg Tyr Leu Gly Leu Leu Phe Gln Val Val Asp Asp Ile
    210                 215                 220 ctc gat gtc aca aaa tct tct gaa gat ttg ggt aag act gca gga aag       720
Leu Asp Val Thr Lys Ser Ser Glu Asp Leu Gly Lys Thr Ala Gly Lys
225                 230                 235                 240 gat ttg gtt agt gat aag gcc act tat ccc aag ctg atg ggt tta gag       768
Asp Leu Val Ser Asp Lys Ala Thr Tyr Pro Lys Leu Met Gly Leu Glu
                245                 250                 255 aaa gca aag gga ttt tct ctt gaa ttg ttg aac aaa gct aag gag gag       816
Lys Ala Lys Gly Phe Ser Leu Glu Leu Leu Asn Lys Ala Lys Glu Glu
            260                 265                 270 tta tca tgc ttc gat cca atg aag gct gca cct ctg ttc ggt ctt gca       864
Leu Ser Cys Phe Asp Pro Met Lys Ala Ala Pro Leu Phe Gly Leu Ala
        275                 280                 285 gat tac atg gca ctc aga cag aat ctc gag cac cac cac cac cac cac       912
Asp Tyr Met Ala Leu Arg Gln Asn Leu Glu His His His His His His
    290                 295                 300 tga                                                                   915

<210> SEQ ID NO 20
<211> LENGTH: 304
<212> TYPE: PRT
<213> ORGANISM: Abies Grandis

<400> SEQUENCE: 20

Met Phe Asp Phe Asn Lys Tyr Met Leu Ser Lys Ala Met Ala Val Thr
1               5                   10                  15

Glu Ala Leu Asp Lys Ala Ile Pro His Ser Tyr Pro Gln Lys Ile His
                20                  25                  30

Glu Ser Met Arg Tyr Ser Leu Leu Ala Gly Gly Lys Arg Val Arg Pro
            35                  40                  45

Val Leu Cys Ile Ala Ala Cys Glu Leu Val Gly Gly Arg Glu Glu Leu
        50                  55                  60

Ala Met Pro Thr Ala Cys Ala Met Glu Met Ile His Thr Met Ser Leu
65                  70                  75                  80

Ile His Asp Asp Leu Pro Cys Met Asp Asn Asp Asp Leu Arg Arg Gly
                85                  90                  95
```

```
Lys Pro Thr Asn His Lys Val Phe Gly Gln Asp Thr Ala Leu Leu Ala
            100                 105                 110

Gly Asp Ala Leu His Ala Phe Ala Phe Glu His Ile Val Ala Phe Thr
        115                 120                 125

Ser Lys Ser Val Gly Ser Asp Gly Ile Leu Arg Ala Val Thr Glu Leu
    130                 135                 140

Ala Arg Ala Thr Gly Pro Gln Gly Ile Met Gly Gly Gln Ile Val Asp
145                 150                 155                 160

Ile Ala Ser Glu Arg Asp Ala Phe Val Asp Leu Gln Thr Leu Glu Trp
                165                 170                 175

Ile His Ile His Lys Thr Ala Val Leu Phe Glu Cys Ala Thr Val Cys
            180                 185                 190

Gly Ala Ile Ile Gly Gly Ala Ser Gly Asp Glu Ile Glu Arg Ile Arg
        195                 200                 205

Arg Phe Ala Arg Tyr Leu Gly Leu Leu Phe Gln Val Val Asp Asp Ile
    210                 215                 220

Leu Asp Val Thr Lys Ser Ser Glu Asp Leu Gly Lys Thr Ala Gly Lys
225                 230                 235                 240

Asp Leu Val Ser Asp Lys Ala Thr Tyr Pro Lys Leu Met Gly Leu Glu
                245                 250                 255

Lys Ala Lys Gly Phe Ser Leu Glu Leu Leu Asn Lys Ala Lys Glu Glu
            260                 265                 270

Leu Ser Cys Phe Asp Pro Met Lys Ala Ala Pro Leu Phe Gly Leu Ala
        275                 280                 285

Asp Tyr Met Ala Leu Arg Gln Asn Leu Glu His His His His His His
    290                 295                 300

<210> SEQ ID NO 21
<211> LENGTH: 1535
<212> TYPE: DNA
<213> ORGANISM: Abies Grandis
<220> FEATURE:
<221> NAME/KEY: CDS
<222> LOCATION: (58)..(1206)

<400> SEQUENCE: 21
tctgcttctg ttggagttga tagcaggaaa aaatcaaagt agaaatagaa caaagat        57 atg gct tat agc ggt atg gcg act agc tac cat ggc ctg cat ttt atg    105
Met Ala Tyr Ser Gly Met Ala Thr Ser Tyr His Gly Leu His Phe Met
1               5                   10                  15 aat att gct act caa gaa tgt aat ttg aag aga ctt tct atc cca tcg    153
Asn Ile Ala Thr Gln Glu Cys Asn Leu Lys Arg Leu Ser Ile Pro Ser
            20                  25                  30 aga cgt ttt cat gga gtt tca cca tca ttg tgg gct tct aat ggc ttc    201
Arg Arg Phe His Gly Val Ser Pro Ser Leu Trp Ala Ser Asn Gly Phe
        35                  40                  45 caa ggc cat tta aag agg gag tta tcc gca aat tca ttt ctg gta tca    249
Gln Gly His Leu Lys Arg Glu Leu Ser Ala Asn Ser Phe Leu Val Ser
    50                  55                  60 tca tct aga tac tca aac aca att gct aag ttt act aat ctg cct gaa    297
Ser Ser Arg Tyr Ser Asn Thr Ile Ala Lys Phe Thr Asn Leu Pro Glu
65                  70                  75                  80 aaa gta aag gag aag gtc att gaa ttt gac ttc aag gag tat cta cgt    345
Lys Val Lys Glu Lys Val Ile Glu Phe Asp Phe Lys Glu Tyr Leu Arg
                85                  90                  95 tcc aag gca atg gca gtg aat gag gca ctg gat agg gct gta cca ctt    393
Ser Lys Ala Met Ala Val Asn Glu Ala Leu Asp Arg Ala Val Pro Leu
```

```
                   100                 105                 110
cgt tat cct gaa aga ata cat gaa gct atg agg tat tct ctt cta gca       441
Arg Tyr Pro Glu Arg Ile His Glu Ala Met Arg Tyr Ser Leu Leu Ala
        115                 120                 125 gga ggg aag agg gtt cgt cct gtt ctg tgc att tca gca tgt gag ctt       489
Gly Gly Lys Arg Val Arg Pro Val Leu Cys Ile Ser Ala Cys Glu Leu
130                 135                 140 gtg gga ggg acc gag gaa gtc gcc atg cca act gcc tgt gca atg gag       537
Val Gly Gly Thr Glu Glu Val Ala Met Pro Thr Ala Cys Ala Met Glu
145                 150                 155                 160 atg atc cac aca atg tct tta att cat gat gac ttg cct tgc atg gac       585
Met Ile His Thr Met Ser Leu Ile His Asp Asp Leu Pro Cys Met Asp
                165                 170                 175 aat gat gat ttt cgc aga ggt aag cct aca aac cac aag gtc ttc ggg       633
Asn Asp Asp Phe Arg Arg Gly Lys Pro Thr Asn His Lys Val Phe Gly
        180                 185                 190 gaa ggc act gct att ctt gca ggg gat gca ctg ctt tca ttt gca ttt       681
Glu Gly Thr Ala Ile Leu Ala Gly Asp Ala Leu Leu Ser Phe Ala Phe
                195                 200                 205 gaa cac att gca gta tcc aca agc aaa tct gtg ggg act gat agg att       729
Glu His Ile Ala Val Ser Thr Ser Lys Ser Val Gly Thr Asp Arg Ile
        210                 215                 220 ttg agg gtg gta tct gaa ttg ggt aga aca ata ggc tcc caa ggg ctt       777
Leu Arg Val Val Ser Glu Leu Gly Arg Thr Ile Gly Ser Gln Gly Leu
225                 230                 235                 240 gtg ggt ggg cag gtt gct gat att acg agt gag ggc gat gct tct gtt       825
Val Gly Gly Gln Val Ala Asp Ile Thr Ser Glu Gly Asp Ala Ser Val
                245                 250                 255 gac ctt gac act ctg gaa tgg att cac att cat aag act gca gtg cta       873
Asp Leu Asp Thr Leu Glu Trp Ile His Ile His Lys Thr Ala Val Leu
        260                 265                 270 ttg gag tgc tca gtt atg tgt ggg gcg atc att agt ggt gct tca gac       921
Leu Glu Cys Ser Val Met Cys Gly Ala Ile Ile Ser Gly Ala Ser Asp
                275                 280                 285 aat gag att gag aga att caa aga tat gcc cgt agc gtg ggg ctt ctg       969
Asn Glu Ile Glu Arg Ile Gln Arg Tyr Ala Arg Ser Val Gly Leu Leu
        290                 295                 300 ttt cag gtt gtt gac gac ata ctc gac gtc acg aaa tca tca aaa gag      1017
Phe Gln Val Val Asp Asp Ile Leu Asp Val Thr Lys Ser Ser Lys Glu
305                 310                 315                 320 ttg ggc aaa act gca gga aag gat ttg atc agt gat aag gcc act tat      1065
Leu Gly Lys Thr Ala Gly Lys Asp Leu Ile Ser Asp Lys Ala Thr Tyr
                325                 330                 335 ccg aag ctg atg ggt tta gag aaa gca aaa caa ttt gct tcg gat ttg      1113
Pro Lys Leu Met Gly Leu Glu Lys Ala Lys Gln Phe Ala Ser Asp Leu
        340                 345                 350 ttg atc aga gct aag gag gat tta tct tgc ttc gac cca atg aag gct      1161
Leu Ile Arg Ala Lys Glu Asp Leu Ser Cys Phe Asp Pro Met Lys Ala
        355                 360                 365 gca cca ttg ttg ggt ctt gca gat tac att gca ttc aga caa aac           1206
Ala Pro Leu Leu Gly Leu Ala Asp Tyr Ile Ala Phe Arg Gln Asn
        370                 375                 380 tgaagagcct ctaaaagtgt tcttatgtat gcgttctgtg ctttgttttt acatctacta    1266
caacctagaa aataacatat gtaacatcat gtctctttga gttgtgatga tggataatag    1326
aatggttcca ataggaagta atgcctggat ctaggtccaa ggaaccagtc ccatgttctt    1386
atgtaggagt tcctttaacc tttagaccaa tttatctttg atgttattct tgttgccaga    1446
gaaaagagtt ctcacagcta agcttagcct ggagaatatc ggctggttgc ttgattcaag    1506
```

```
<210> SEQ ID NO 22
<211> LENGTH: 383
<212> TYPE: PRT
<213> ORGANISM: Abies Grandis

<400> SEQUENCE: 22
```

| | | | | | | | | | | | | | | |
|---|---|---|---|---|---|---|---|---|---|---|---|---|---|---|
| Met | Ala | Tyr | Ser | Gly | Met | Ala | Thr | Ser | Tyr | His | Gly | Leu | His | Phe | Met |
| 1 | | | | 5 | | | | | 10 | | | | | 15 | |
| Asn | Ile | Ala | Thr | Gln | Glu | Cys | Asn | Leu | Lys | Arg | Leu | Ser | Ile | Pro | Ser |
| | | | 20 | | | | | 25 | | | | | 30 | | |
| Arg | Arg | Phe | His | Gly | Val | Ser | Pro | Ser | Leu | Trp | Ala | Ser | Asn | Gly | Phe |
| | | | 35 | | | | | 40 | | | | | 45 | | |
| Gln | Gly | His | Leu | Lys | Arg | Glu | Leu | Ser | Ala | Asn | Ser | Phe | Leu | Val | Ser |
| | 50 | | | | | 55 | | | | | 60 | | | | |
| Ser | Ser | Arg | Tyr | Ser | Asn | Thr | Ile | Ala | Lys | Phe | Thr | Asn | Leu | Pro | Glu |
| 65 | | | | | 70 | | | | | 75 | | | | | 80 |
| Lys | Val | Lys | Glu | Lys | Val | Ile | Glu | Phe | Asp | Phe | Lys | Glu | Tyr | Leu | Arg |
| | | | | 85 | | | | | 90 | | | | | 95 | |
| Ser | Lys | Ala | Met | Ala | Val | Asn | Glu | Ala | Leu | Asp | Arg | Ala | Val | Pro | Leu |
| | | | 100 | | | | | 105 | | | | | 110 | | |
| Arg | Tyr | Pro | Glu | Arg | Ile | His | Glu | Ala | Met | Arg | Tyr | Ser | Leu | Leu | Ala |
| | | | 115 | | | | | 120 | | | | | 125 | | |
| Gly | Gly | Lys | Arg | Val | Arg | Pro | Val | Leu | Cys | Ile | Ser | Ala | Cys | Glu | Leu |
| | 130 | | | | | 135 | | | | | 140 | | | | |
| Val | Gly | Gly | Thr | Glu | Glu | Val | Ala | Met | Pro | Thr | Ala | Cys | Ala | Met | Glu |
| 145 | | | | | 150 | | | | | 155 | | | | | 160 |
| Met | Ile | His | Thr | Met | Ser | Leu | Ile | His | Asp | Asp | Leu | Pro | Cys | Met | Asp |
| | | | | 165 | | | | | 170 | | | | | 175 | |
| Asn | Asp | Asp | Phe | Arg | Arg | Gly | Lys | Pro | Thr | Asn | His | Lys | Val | Phe | Gly |
| | | | 180 | | | | | 185 | | | | | 190 | | |
| Glu | Gly | Thr | Ala | Ile | Leu | Ala | Gly | Asp | Ala | Leu | Leu | Ser | Phe | Ala | Phe |
| | | | 195 | | | | | 200 | | | | | 205 | | |
| Glu | His | Ile | Ala | Val | Ser | Thr | Ser | Lys | Ser | Val | Gly | Thr | Asp | Arg | Ile |
| | 210 | | | | | 215 | | | | | 220 | | | | |
| Leu | Arg | Val | Val | Ser | Glu | Leu | Gly | Arg | Thr | Ile | Gly | Ser | Gln | Gly | Leu |
| 225 | | | | | 230 | | | | | 235 | | | | | 240 |
| Val | Gly | Gly | Gln | Val | Ala | Asp | Ile | Thr | Ser | Glu | Gly | Asp | Ala | Ser | Val |
| | | | | 245 | | | | | 250 | | | | | 255 | |
| Asp | Leu | Asp | Thr | Leu | Glu | Trp | Ile | His | Ile | His | Lys | Thr | Ala | Val | Leu |
| | | | 260 | | | | | 265 | | | | | 270 | | |
| Leu | Glu | Cys | Ser | Val | Met | Cys | Gly | Ala | Ile | Ile | Ser | Gly | Ala | Ser | Asp |
| | | | 275 | | | | | 280 | | | | | 285 | | |
| Asn | Glu | Ile | Glu | Arg | Ile | Gln | Arg | Tyr | Ala | Arg | Ser | Val | Gly | Leu | Leu |
| | 290 | | | | | 295 | | | | | 300 | | | | |
| Phe | Gln | Val | Val | Asp | Asp | Ile | Leu | Asp | Val | Thr | Lys | Ser | Ser | Lys | Glu |
| 305 | | | | | 310 | | | | | 315 | | | | | 320 |
| Leu | Gly | Lys | Thr | Ala | Gly | Lys | Asp | Leu | Ile | Ser | Asp | Lys | Ala | Thr | Tyr |
| | | | | 325 | | | | | 330 | | | | | 335 | |
| Pro | Lys | Leu | Met | Gly | Leu | Glu | Lys | Ala | Lys | Gln | Phe | Ala | Ser | Asp | Leu |
| | | | 340 | | | | | 345 | | | | | 350 | | |
| Leu | Ile | Arg | Ala | Lys | Glu | Asp | Leu | Ser | Cys | Phe | Asp | Pro | Met | Lys | Ala |
| | | | 355 | | | | | 360 | | | | | 365 | | |

Ala Pro Leu Leu Gly Leu Ala Asp Tyr Ile Ala Phe Arg Gln Asn
    370             375             380

<210> SEQ ID NO 23
<211> LENGTH: 891
<212> TYPE: DNA
<213> ORGANISM: Abies Grandis
<220> FEATURE:
<221> NAME/KEY: CDS
<222> LOCATION: (1)..(888)

<400> SEQUENCE: 23

```
atg ttt gac ttc aag gag tat cta cgt tcc aag gca atg gca gtg aat      48
Met Phe Asp Phe Lys Glu Tyr Leu Arg Ser Lys Ala Met Ala Val Asn
1               5                   10                  15 gag gca ctg gat agg gct gta cca ctt cgt tat cct gaa aga ata cat      96
Glu Ala Leu Asp Arg Ala Val Pro Leu Arg Tyr Pro Glu Arg Ile His
            20                  25                  30 gaa gct atg agg tat tct ctt cta gca gga ggg aag agg gtt cgt cct     144
Glu Ala Met Arg Tyr Ser Leu Leu Ala Gly Gly Lys Arg Val Arg Pro
        35                  40                  45 gtt ctg tgc att tca gca tgt gag ctt gtg gga ggg acc gag gaa gtc     192
Val Leu Cys Ile Ser Ala Cys Glu Leu Val Gly Gly Thr Glu Glu Val
    50                  55                  60 gcc atg cca act gcc tgt gca atg gag atg atc cac aca atg tct tta     240
Ala Met Pro Thr Ala Cys Ala Met Glu Met Ile His Thr Met Ser Leu
65                  70                  75                  80 att cat gat gac ttg cct tgc atg gac aat gat gat ttt cgc aga ggt     288
Ile His Asp Asp Leu Pro Cys Met Asp Asn Asp Asp Phe Arg Arg Gly
                85                  90                  95 aag cct aca aac cac aag gtc ttc ggg gaa ggc act gct att ctt gca     336
Lys Pro Thr Asn His Lys Val Phe Gly Glu Gly Thr Ala Ile Leu Ala
            100                 105                 110 ggg gat gca ctg ctt tca ttt gca ttt gaa cac att gca gta tcc aca     384
Gly Asp Ala Leu Leu Ser Phe Ala Phe Glu His Ile Ala Val Ser Thr
        115                 120                 125 agc aaa tct gtg ggg act gat agg att ttg agg gtg gta tct gaa ttg     432
Ser Lys Ser Val Gly Thr Asp Arg Ile Leu Arg Val Val Ser Glu Leu
    130                 135                 140 ggt aga aca ata ggc tcc caa ggg ctt gtg ggt ggg cag gtt gct gat     480
Gly Arg Thr Ile Gly Ser Gln Gly Leu Val Gly Gly Gln Val Ala Asp
145                 150                 155                 160 att acg agt gag ggc gat gct tct gtt gac ctt gac act ctg gaa tgg     528
Ile Thr Ser Glu Gly Asp Ala Ser Val Asp Leu Asp Thr Leu Glu Trp
                165                 170                 175 att cac att cat aag act gca gtg cta ttg gag tgc tca gtt atg tgt     576
Ile His Ile His Lys Thr Ala Val Leu Leu Glu Cys Ser Val Met Cys
            180                 185                 190 ggg gcg atc att agt ggt gct tca gac aat gag att gag aga att caa     624
Gly Ala Ile Ile Ser Gly Ala Ser Asp Asn Glu Ile Glu Arg Ile Gln
        195                 200                 205 aga tat gcc cgt agc gtg ggg ctt ctg ttt cag gtt gtt gac gac ata     672
Arg Tyr Ala Arg Ser Val Gly Leu Leu Phe Gln Val Val Asp Asp Ile
    210                 215                 220 ctc gac gtc acg aaa tca tca aaa gag ttg ggc aaa act gca gga aag     720
Leu Asp Val Thr Lys Ser Ser Lys Glu Leu Gly Lys Thr Ala Gly Lys
225                 230                 235                 240 gat ttg atc agt gat aag gcc act tat ccg aag ctg atg ggt tta gag     768
Asp Leu Ile Ser Asp Lys Ala Thr Tyr Pro Lys Leu Met Gly Leu Glu
                245                 250                 255
```

```
aaa gca aaa caa ttt gct tcg gat ttg ttg atc aga gct aag gag gat        816
Lys Ala Lys Gln Phe Ala Ser Asp Leu Leu Ile Arg Ala Lys Glu Asp
        260                 265                 270 tta tct tgc ttc gac cca atg aag gct gca cca ttg ttg ggt ctt gca        864
Leu Ser Cys Phe Asp Pro Met Lys Ala Ala Pro Leu Leu Gly Leu Ala
    275                 280                 285 gat tac att gca ttc aga caa aac tga                                    891
Asp Tyr Ile Ala Phe Arg Gln Asn
        290                 295
```

<210> SEQ ID NO 24
<211> LENGTH: 296
<212> TYPE: PRT
<213> ORGANISM: Abies Grandis

<400> SEQUENCE: 24

```
Met Phe Asp Phe Lys Glu Tyr Leu Arg Ser Lys Ala Met Ala Val Asn
1               5                   10                  15

Glu Ala Leu Asp Arg Ala Val Pro Leu Arg Tyr Pro Glu Arg Ile His
            20                  25                  30

Glu Ala Met Arg Tyr Ser Leu Leu Ala Gly Gly Lys Arg Val Arg Pro
        35                  40                  45

Val Leu Cys Ile Ser Ala Cys Glu Leu Val Gly Gly Thr Glu Glu Val
    50                  55                  60

Ala Met Pro Thr Ala Cys Ala Met Glu Met Ile His Thr Met Ser Leu
65                  70                  75                  80

Ile His Asp Asp Leu Pro Cys Met Asp Asn Asp Asp Phe Arg Arg Gly
                85                  90                  95

Lys Pro Thr Asn His Lys Val Phe Gly Glu Gly Thr Ala Ile Leu Ala
            100                 105                 110

Gly Asp Ala Leu Leu Ser Phe Ala Phe Glu His Ile Ala Val Ser Thr
        115                 120                 125

Ser Lys Ser Val Gly Thr Asp Arg Ile Leu Arg Val Val Ser Glu Leu
    130                 135                 140

Gly Arg Thr Ile Gly Ser Gln Gly Leu Val Gly Gly Gln Val Ala Asp
145                 150                 155                 160

Ile Thr Ser Glu Gly Asp Ala Ser Val Asp Leu Asp Thr Leu Glu Trp
                165                 170                 175

Ile His Ile His Lys Thr Ala Val Leu Leu Glu Cys Ser Val Met Cys
            180                 185                 190

Gly Ala Ile Ile Ser Gly Ala Ser Asp Asn Glu Ile Glu Arg Ile Gln
        195                 200                 205

Arg Tyr Ala Arg Ser Val Gly Leu Leu Phe Gln Val Val Asp Asp Ile
    210                 215                 220

Leu Asp Val Thr Lys Ser Ser Lys Glu Leu Gly Lys Thr Ala Gly Lys
225                 230                 235                 240

Asp Leu Ile Ser Asp Lys Ala Thr Tyr Pro Lys Leu Met Gly Leu Glu
                245                 250                 255

Lys Ala Lys Gln Phe Ala Ser Asp Leu Leu Ile Arg Ala Lys Glu Asp
            260                 265                 270

Leu Ser Cys Phe Asp Pro Met Lys Ala Ala Pro Leu Leu Gly Leu Ala
        275                 280                 285

Asp Tyr Ile Ala Phe Arg Gln Asn
    290                 295
```

<210> SEQ ID NO 25

```
<211> LENGTH: 915
<212> TYPE: DNA
<213> ORGANISM: Abies Grandis
<220> FEATURE:
<221> NAME/KEY: CDS
<222> LOCATION: (1)..(912)

<400> SEQUENCE: 25
```

| | | | | | | | | | | | | | | | | |
|---|---|---|---|---|---|---|---|---|---|---|---|---|---|---|---|---|
| atg | ttt | gac | ttc | aag | gag | tat | cta | cgt | tcc | aag | gca | atg | gca | gtg | aat | 48 |
| Met | Phe | Asp | Phe | Lys | Glu | Tyr | Leu | Arg | Ser | Lys | Ala | Met | Ala | Val | Asn | |
| 1 | | | | 5 | | | | | 10 | | | | | 15 | | |
| gag | gca | ctg | gat | agg | gct | gta | cca | ctt | cgt | tat | cct | gaa | aga | ata | cat | 96 |
| Glu | Ala | Leu | Asp | Arg | Ala | Val | Pro | Leu | Arg | Tyr | Pro | Glu | Arg | Ile | His | |
| | | | 20 | | | | | 25 | | | | | 30 | | | |
| gaa | gct | atg | agg | tat | tct | ctt | cta | gca | gga | ggg | aag | agg | gtt | cgt | cct | 144 |
| Glu | Ala | Met | Arg | Tyr | Ser | Leu | Leu | Ala | Gly | Gly | Lys | Arg | Val | Arg | Pro | |
| | | 35 | | | | | 40 | | | | | 45 | | | | |
| gtt | ctg | tgc | att | tca | gca | tgt | gag | ctt | gtg | gga | ggg | acc | gag | gaa | gtc | 192 |
| Val | Leu | Cys | Ile | Ser | Ala | Cys | Glu | Leu | Val | Gly | Gly | Thr | Glu | Glu | Val | |
| | 50 | | | | | 55 | | | | | 60 | | | | | |
| gcc | atg | cca | act | gcc | tgt | gca | atg | gag | atg | atc | cac | aca | atg | tct | tta | 240 |
| Ala | Met | Pro | Thr | Ala | Cys | Ala | Met | Glu | Met | Ile | His | Thr | Met | Ser | Leu | |
| 65 | | | | | 70 | | | | | 75 | | | | | 80 | |
| att | cat | gat | gac | ttg | cct | tgc | atg | gac | aat | gat | gat | ttt | cgc | aga | ggt | 288 |
| Ile | His | Asp | Asp | Leu | Pro | Cys | Met | Asp | Asn | Asp | Asp | Phe | Arg | Arg | Gly | |
| | | | | 85 | | | | | 90 | | | | | 95 | | |
| aag | cct | aca | aac | cac | aag | gtc | ttc | ggg | gaa | ggc | act | gct | att | ctt | gca | 336 |
| Lys | Pro | Thr | Asn | His | Lys | Val | Phe | Gly | Glu | Gly | Thr | Ala | Ile | Leu | Ala | |
| | | | 100 | | | | | 105 | | | | | 110 | | | |
| ggg | gat | gca | ctg | ctt | tca | ttt | gca | ttt | gaa | cac | att | gca | gta | tcc | aca | 384 |
| Gly | Asp | Ala | Leu | Leu | Ser | Phe | Ala | Phe | Glu | His | Ile | Ala | Val | Ser | Thr | |
| | | 115 | | | | | 120 | | | | | 125 | | | | |
| agc | aaa | tct | gtg | ggg | act | gat | agg | att | ttg | agg | gtg | gta | tct | gaa | ttg | 432 |
| Ser | Lys | Ser | Val | Gly | Thr | Asp | Arg | Ile | Leu | Arg | Val | Val | Ser | Glu | Leu | |
| | 130 | | | | | 135 | | | | | 140 | | | | | |
| ggt | aga | aca | ata | ggc | tcc | caa | ggg | ctt | gtg | ggt | ggg | cag | gtt | gct | gat | 480 |
| Gly | Arg | Thr | Ile | Gly | Ser | Gln | Gly | Leu | Val | Gly | Gly | Gln | Val | Ala | Asp | |
| 145 | | | | | 150 | | | | | 155 | | | | | 160 | |
| att | acg | agt | gag | ggc | gat | gct | tct | gtt | gac | ctt | gac | act | ctg | gaa | tgg | 528 |
| Ile | Thr | Ser | Glu | Gly | Asp | Ala | Ser | Val | Asp | Leu | Asp | Thr | Leu | Glu | Trp | |
| | | | | 165 | | | | | 170 | | | | | 175 | | |
| att | cac | att | cat | aag | act | gca | gtg | cta | ttg | gag | tgc | tca | gtt | atg | tgt | 576 |
| Ile | His | Ile | His | Lys | Thr | Ala | Val | Leu | Leu | Glu | Cys | Ser | Val | Met | Cys | |
| | | | 180 | | | | | 185 | | | | | 190 | | | |
| ggg | gcg | atc | att | agt | ggt | gct | tca | gac | aat | gag | att | gag | aga | att | caa | 624 |
| Gly | Ala | Ile | Ile | Ser | Gly | Ala | Ser | Asp | Asn | Glu | Ile | Glu | Arg | Ile | Gln | |
| | | 195 | | | | | 200 | | | | | 205 | | | | |
| aga | tat | gcc | cgt | agc | gtg | ggg | ctt | ctg | ttt | cag | gtt | gtt | gac | gac | ata | 672 |
| Arg | Tyr | Ala | Arg | Ser | Val | Gly | Leu | Leu | Phe | Gln | Val | Val | Asp | Asp | Ile | |
| | 210 | | | | | 215 | | | | | 220 | | | | | |
| ctc | gac | gtc | acg | aaa | tca | tca | aaa | gag | ttg | ggc | aaa | act | gca | gga | aag | 720 |
| Leu | Asp | Val | Thr | Lys | Ser | Ser | Lys | Glu | Leu | Gly | Lys | Thr | Ala | Gly | Lys | |
| 225 | | | | | 230 | | | | | 235 | | | | | 240 | |
| gat | ttg | atc | agt | gat | aag | gcc | act | tat | ccg | aag | ctg | atg | ggt | tta | gag | 768 |
| Asp | Leu | Ile | Ser | Asp | Lys | Ala | Thr | Tyr | Pro | Lys | Leu | Met | Gly | Leu | Glu | |
| | | | | 245 | | | | | 250 | | | | | 255 | | |
| aaa | gca | aaa | caa | ttt | gct | tcg | gat | ttg | ttg | atc | aga | gct | aag | gag | gat | 816 |
| Lys | Ala | Lys | Gln | Phe | Ala | Ser | Asp | Leu | Leu | Ile | Arg | Ala | Lys | Glu | Asp | |
| | | | 260 | | | | | 265 | | | | | 270 | | | |
| tta | tct | tgc | ttc | gac | cca | atg | aag | gct | gca | cca | ttg | ttg | ggt | ctt | gca | 864 |
| Leu | Ser | Cys | Phe | Asp | Pro | Met | Lys | Ala | Ala | Pro | Leu | Leu | Gly | Leu | Ala | |

```
                    275                 280                 285
gat  tac  att  gca  ttc  aga  caa  aac  ctc  gag  cac  cac  cac  cac  cac        912
Asp  Tyr  Ile  Ala  Phe  Arg  Gln  Asn  Leu  Glu  His  His  His  His  His
         290                 295                 300 tga                                                                              915
```

<210> SEQ ID NO 26
<211> LENGTH: 304
<212> TYPE: PRT
<213> ORGANISM: Abies Grandis

<400> SEQUENCE: 26

```
Met Phe Asp Phe Lys Glu Tyr Leu Arg Ser Lys Ala Met Ala Val Asn
1               5                   10                  15

Glu Ala Leu Asp Arg Ala Val Pro Leu Arg Tyr Pro Glu Arg Ile His
            20                  25                  30

Glu Ala Met Arg Tyr Ser Leu Leu Ala Gly Gly Lys Arg Val Arg Pro
        35                  40                  45

Val Leu Cys Ile Ser Ala Cys Glu Leu Val Gly Gly Thr Glu Glu Val
50                  55                  60

Ala Met Pro Thr Ala Cys Ala Met Glu Met Ile His Thr Met Ser Leu
65                  70                  75                  80

Ile His Asp Asp Leu Pro Cys Met Asp Asn Asp Phe Arg Arg Gly
                85                  90                  95

Lys Pro Thr Asn His Lys Val Phe Gly Glu Gly Thr Ala Ile Leu Ala
            100                 105                 110

Gly Asp Ala Leu Leu Ser Phe Ala Phe Glu His Ile Ala Val Ser Thr
        115                 120                 125

Ser Lys Ser Val Gly Thr Asp Arg Ile Leu Arg Val Val Ser Glu Leu
130                 135                 140

Gly Arg Thr Ile Gly Ser Gln Gly Leu Val Gly Gln Val Ala Asp
145                 150                 155                 160

Ile Thr Ser Glu Gly Asp Ala Ser Val Asp Leu Asp Thr Leu Glu Trp
                165                 170                 175

Ile His Ile His Lys Thr Ala Val Leu Leu Glu Cys Ser Val Met Cys
            180                 185                 190

Gly Ala Ile Ile Ser Gly Ala Ser Asp Asn Glu Ile Glu Arg Ile Gln
        195                 200                 205

Arg Tyr Ala Arg Ser Val Gly Leu Leu Phe Gln Val Val Asp Asp Ile
210                 215                 220

Leu Asp Val Thr Lys Ser Ser Lys Glu Leu Gly Lys Thr Ala Gly Lys
225                 230                 235                 240

Asp Leu Ile Ser Asp Lys Ala Thr Tyr Pro Lys Leu Met Gly Leu Glu
                245                 250                 255

Lys Ala Lys Gln Phe Ala Ser Asp Leu Leu Ile Arg Ala Lys Glu Asp
            260                 265                 270

Leu Ser Cys Phe Asp Pro Met Lys Ala Ala Pro Leu Leu Gly Leu Ala
        275                 280                 285

Asp Tyr Ile Ala Phe Arg Gln Asn Leu Glu His His His His His
290                 295                 300
```

<210> SEQ ID NO 27
<211> LENGTH: 30
<212> TYPE: DNA
<213> ORGANISM: Artificial Sequence
<220> FEATURE:

-continued

```
<223> OTHER INFORMATION: Oligonucleotide Primer

<400> SEQUENCE: 27
gaaatagaac aaacatatgg cttacagttg                                    30

<210> SEQ ID NO 28
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 28
ggaaaaggcc catatgtttg atttcaagg                                     29

<210> SEQ ID NO 29
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 29
gaacacattt ctcgagcttt tcagttc                                       27

<210> SEQ ID NO 30
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 30
catttcgcag gcctcgaggt tctgtcttaa tg                                 32

<210> SEQ ID NO 31
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 31
ctaatcatat aaagagcata tggcttacag tgc                                33

<210> SEQ ID NO 32
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 32
ggaagaaggc ccatatgttt gatttc                                        26

<210> SEQ ID NO 33
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 33
caaacaagaa cgctcgagga ggctcttc                                      28
```

```
<210> SEQ ID NO 34
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 34
gctttgagga ggctcgagat tttgtctg                                    28

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 35
ggcttacagt catatggtac gtagc                                       25

<210> SEQ ID NO 36
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 36
ggaagaaggt ccatatgttt gatttc                                      26

<210> SEQ ID NO 37
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 37
ggaacgattt tactcgagtt ttcaattc                                    28

<210> SEQ ID NO 38
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 38
ggaacgattt tactcgagtt ttcaattc                                    28

<210> SEQ ID NO 39
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 39
gaaatagaac aaacatatgg cttatagc                                    28

<210> SEQ ID NO 40
<211> LENGTH: 29
<212> TYPE: DNA
<213> ORGANISM: Artificial Sequence
<220> FEATURE:
<223> OTHER INFORMATION: Oligonucleotide Primer
```

```
<400> SEQUENCE: 40
ggagaaggtc catatgtttg acttcaagg                                      29

<210> SEQ ID NO 41
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 41
cataagaaca cttctcgagg ctcttcagtt ttg                                 33

<210> SEQ ID NO 42
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 42
cacttttaga ggctcgaggt tttgtctg                                       28
```

GERANYL DIPHOSPHATE SYNTHASE MOLECULES, AND NUCLEIC ACID MOLECULES ENCODING SAME

CROSS-REFERENCES TO RELATED APPLICATIONS

This application is a continuation of PCT/US03/23159, filed Jul. 23, 2003, which claims the benefit of U.S. Provisional Application No. 60/400,081, filed Jul. 31, 2002.

STATEMENT OF GOVERNMENT LICENSE RIGHTS

The invention was made with government support under Contract No. DE-FG03-96ER2012 awarded by the Department of Energy.

FIELD OF THE INVENTION

The present invention relates to geranyl diphosphate synthase proteins, to nucleic acid molecules that encode a geranyl diphosphate synthase protein, and to methods for altering the level of expression of geranyl diphosphate synthase in a host cell, such as a plant cell.

BACKGROUND OF THE INVENTION

The monoterpenes are a large family of plant natural products that function as defensive agents, pollination attractants and allelopathic compounds (J. B. Harborne, in J. B. Harborne and F. A. Tomas-Barberan (eds.), *Ecological Chemistry and Biochemistry of Plant Terpenoids*, Vol. 31, Clarendon Press, Oxford, 1991, pp. 396-426; J. H. Langenheim, *J. Chem. Ecol.* 20:1223-1280, 1994). Over 500 naturally occurring monoterpenes have been identified (J. Buckingham, *Dictionary of Natural Products on CD-ROM*, Ver. 6.1, Chapman & Hall, London, 1998), a number of which are of commercial importance as flavors and fragrances, pharmaceuticals, insecticides and synthetic intermediates (D. F. Zinkel and J. Russell (eds.), *Naval Stores: Production, Chemistry, Utilization*, Pulp Chemical Association, New York, 1989, pp. 477-572; B. M. Lawrence, *Perfum. Flavor* 17:15-28, 1992; F. A. Dawson, *Naval Stores Rev. March/April* 1994, pp. 6-12).

The universal precursor of the monoterpenes is geranyl diphosphate (GPP) produced by geranyl diphosphate synthase (GPPS) which catalyzes the condensation of isopentenyl diphosphate (IPP) and dimethylallyl diphosphate (DMAPP) to the $C_{10}$ product (see THE FIGURE). This enzyme is similar to farnesyl diphosphate synthase (FPPS) which condenses two molecules of IPP with DMAPP to form the $C_{15}$ precursor of the sesquiterpenes and triterpenes, and to geranylgeranyl diphosphate synthase (GGPPS) which condenses three molecules of IPP with DMAPP to form the $C_{20}$ precursor of diterpenes and tetraterpenes (see THE FIGURE). These enzymes, referred to collectively as short-chain prenyltransferases, function at the branch-points of isoprenoid metabolism and are considered to play a regulatory role in controlling the flux distribution of IPP into the various terpenoid families (J. Gershenzon and R. Croteau, in T. S. Moore, Jr. (ed.), *Lipid Metabolism in Plants*, CRC Press, Boca Raton, Fla., 1993, pp. 339-388).

Given the importance of GPPS in plant isoprenoid metabolism, there is a continuing need to isolate additional types of GPPS proteins, and nucleic acid molecules that encode GPPS proteins, to facilitate genetic manipulation of plants to optimize, or otherwise alter, plant isoprenoid metabolism. In this regard, an unsuccessful attempt was made to purify a GPPS from *A. grandis* which resulted in only a 15-fold purification of the enzyme with 88% loss of enzymatic activity. The partially purified enzyme was not visible by SDS-PAGE analysis (D. Tholl et al., *Arch. Biochem. Biophys.* 386:233-242, 2001).

SUMMARY OF THE INVENTION

In accordance with the foregoing, cDNA molecules encoding novel geranyl diphosphate synthase proteins were isolated from Grand fir (*Abies grandis*). Thus, in one aspect, the present invention provides isolated nucleic acid molecules that each encode a geranyl diphosphate synthase protein, wherein each isolated nucleic acid molecule hybridizes to a nucleic acid molecule consisting of the sequence set forth in SEQ ID NO:1 under conditions of 5×SSC at 45° C. for one hour. The nucleic acid sequence set forth in SEQ ID NO:1 is the complement of the nucleic acid sequence set forth in SEQ ID NO:2 that encodes the geranyl diphosphate synthase protein having the amino acid sequence set forth in SEQ ID NO:3. Other exemplary nucleic acid molecules of the invention that encode a geranyl diphosphate synthase protein have the nucleic acid sequences set forth in SEQ ID NO:4 (encoding the geranyl diphosphate synthase protein having the amino acid sequence set forth in SEQ ID NO:5), and in SEQ ID NO:6 (encoding the geranyl diphosphate synthase protein having the amino acid sequence set forth in SEQ ID NO:7).

In another aspect, the present invention provides vectors that each include a nucleic acid molecule that encodes a geranyl diphosphate synthase protein, wherein the nucleic acid molecule hybridizes to a nucleic acid molecule consisting of the sequence set forth in SEQ ID NO:1 under conditions of 5×SSC at 45° C. for one hour.

In another aspect, the present invention provides host cells that include a vector comprising a nucleic acid molecule that encodes a geranyl diphosphate synthase protein, wherein the nucleic acid molecule hybridizes to a nucleic acid molecule consisting of the sequence set forth in SEQ ID NO:1 under conditions of 5×SSC at 45° C. for one hour.

In another aspect, the present invention provides methods for increasing the level of geranyl diphosphate synthase in a living cell, the methods each comprising the step of introducing into a living cell an expression vector comprising a nucleic acid molecule that encodes a geranyl diphosphate synthase protein, under conditions that enable expression of the geranyl diphosphate synthase protein, wherein the nucleic acid molecule hybridizes to a nucleic acid molecule consisting of the sequence set forth in SEQ ID NO:1 under conditions of 5×SSC at 45° C. for one hour.

In another aspect, the present invention provides methods for decreasing the level of geranyl diphosphate synthase in a living cell, the methods each comprising the step of introducing into a living cell an expression vector comprising a nucleic acid molecule that hybridizes to a nucleic acid molecule consisting of the sequence set forth in SEQ ID NO:2, under conditions of 5×SSC at 45° C. for one hour, under conditions that enable expression of the nucleic acid molecule.

In another aspect, the present invention provides cultured plant tissue comprising a vector comprising a nucleic acid molecule that encodes a geranyl diphosphate synthase protein, wherein the nucleic acid molecule hybridizes to a nucleic acid molecule consisting of the sequence set forth in SEQ ID NO:1 under conditions of 5×SSC at 45° C. for one hour. For example, the cultured plant tissue can be of the genus *Abies*.

In another aspect, the present invention provides transgenic plants that each comprise an expression vector comprising a nucleic acid molecule that encodes a geranyl diphosphate synthase protein, wherein the nucleic acid molecule hybridizes to a nucleic acid molecule consisting of the sequence set forth in SEQ ID NO:1 under conditions of 5×SSC at 45° C. for one hour. Additionally, the present invention provides transgenic plants that each comprise an expression vector comprising a nucleic acid molecule that hybridizes to a nucleic acid molecule consisting of the sequence set forth in SEQ ID NO:2, under conditions of 5×SSC at 45° C. for one hour.

In another aspect, the present invention provides methods for increasing the level of geranyl diphosphate synthase in a living cell, the methods each comprising introducing into a living cell an expression vector comprising a nucleic acid molecule that encodes a geranyl diphosphate synthase protein under conditions that enable expression of the geranyl diphosphate synthase protein, wherein the nucleic acid molecule hybridizes to a nucleic acid molecule consisting of the sequence set forth in SEQ ID NO:1 under conditions of 5×SSC at 45° C. for one hour.

In another aspect, the present invention provides methods for decreasing the level of geranyl diphosphate synthase in a living cell, the methods each comprising introducing into a living cell an expression vector comprising a nucleic acid molecule, that hybridizes to a nucleic acid molecule consisting of the sequence set forth in SEQ ID NO:2, under conditions of 5×SSC at 45° C. for one hour, under conditions that enable expression of the nucleic acid molecule.

In another aspect, the present invention provides isolated geranyl diphosphate synthase proteins that are at least 70% identical (e.g., at least 80% identical, or at least 90% identical, or at least 95% identical, at least 99% identical) to a geranyl diphosphate synthase protein consisting of the amino acid sequence set forth in SEQ ID NO:3. The present invention also provides isolated geranyl diphosphate synthase proteins that are at least 70% identical (e.g., at least 80% identical, or at least 90% identical, or at least 95% identical, at least 99% identical) to a geranyl diphosphate synthase protein consisting of the amino acid sequence set forth in SEQ ID NO:10.

The isolated nucleic acid molecules of the invention can be introduced into living cells and expressed therein to produce geranyl diphosphate synthase, thereby increasing the amount of geranyl diphosphate synthase in the cells, and increasing production of any natural product for which geranyl diphosphate is a precursor (e.g., prenylated aromatics, such as shikonin, or prenylated alkaloids, such as vinchristine). Thus, for example, the isolated nucleic acid molecules of the invention can be introduced into living plant cells, whole plants regenerated therefrom to yield plants that have an elevated level of geranyl diphosphate synthase, thereby increasing metabolic flux toward monoterpenes in an essential oil-producing plant (e.g., mint) to improve scent, or improve reproductive capability; or increasing metabolic flux toward turpentine in conifers for improved defense and/or enhanced resin production.

The vectors of the invention are useful, for example, for introducing the nucleic acid molecules of the invention into a living cell (e.g., introducing a nucleic acid molecule encoding geranyl diphosphate synthase into a plant cell, and regenerating one or more plants therefrom, wherein the regenerated plant(s) produce elevated levels of geranyl diphosphate synthase and, consequently, elevated levels of one, or more, chemical substance(s) for which geranyl diphosphate is a precursor). The isolated geranyl diphosphate synthase proteins are useful, for example, for producing GPP in vitro. The host cells of the invention are useful, for example, for producing geranyl diphosphate synthase protein which can be purified therefrom, or for producing chemical products for which geranyl diphosphate is a precursor. Thus, for example, some prokaryotic host cells of the invention can be cultured and one or more chemical products, for which geranyl diphosphate is a precursor, can be purified therefrom. Again by way of example, plants comprising a vector of the invention can be used to produce one or more chemical products for which geranyl diphosphate is a precursor. The product(s) may be purified therefrom if so desired.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

THE FIGURE shows the biosynthetic pathway for plant isoprenoids, including monoterpenes, sesquiterpenes and diterpenes.

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al., *Molecular Cloning: A Laboratory Manual*, 2$^{nd}$ ed., Cold Spring Harbor Press, Plainsview, New York (1989), and Ausubel et al., *Current Protocols in Molecular Biology* (Supplement 47), John Wiley & Sons, New York (1999), for definitions and terms of the art.

As used herein, the term "isolated", when used with respect to a nucleic acid molecule of the invention means a nucleic acid molecule that is substantially free from cellular components that are associated with the nucleic acid molecule as it is found in nature. As used in this context, the term "substantially free from cellular components" means that the nucleic acid molecule is purified to a purity level of greater than 80% (such as greater than 90%, greater than 95%, or greater than 99%). Moreover, the term "isolated", when used with respect to a nucleic acid molecule of the invention, includes nucleic acid molecules which do not naturally occur, and have been produced by synthetic means. An isolated nucleic acid molecule generally resolves as a single, predominant, band by gel electrophoresis, and yields a nucleotide sequence profile consistent with the presence of a predominant nucleic acid molecule.

As used herein, the term "isolated", when used with respect to a protein of the invention means a protein that is substantially free from cellular components that are associated with the protein as it is found in nature. As used in this context, the term "substantially free from cellular components" means that the protein is purified to a purity level of greater than 80% (such as greater than 90%, greater than 95%, or greater than 99%). Moreover, the term "isolated", when used with respect to a protein of the invention, includes proteins which do not naturally occur, and have been produced by synthetic means. An isolated protein generally resolves as a single, predominant, band by gel electrophoresis, and yields an amino acid sequence profile consistent with the presence of a predominant protein molecule.

The term "geranyl diphosphate synthase" is used herein to mean an enzyme that catalyzes the condensation of dimethylallyl diphosphate (DMAPP) and isopentenyl diphosphate (IPP) to form geranyl diphosphate (GPP) as the principal reaction product (i.e., at least 50% of the reaction product(s) is GPP).

The term "vector" refers to a nucleic acid molecule, usually double-stranded DNA, which may have inserted into it another nucleic acid molecule (the insert nucleic acid molecule) such as a nucleic acid molecule of the present invention. The vector is used to transport the insert nucleic acid molecule into a suitable host cell. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. Some vectors are expression vectors that include nucleic acid sequence elements required to direct the transcription of the insert nucleic acid molecule. The term "vector" includes the T-DNA of a Ti plasmid.

The abbreviation "SSC" refers to a buffer used in nucleic acid hybridization solutions. One liter of the 20×(twenty times concentrate) stock SSC buffer solution (pH 7.0) contains 175.3 g sodium chloride and 88.2 g sodium citrate.

As described more fully in Example 1, the present inventors used a portion of a *Taxus canadensis* GGPP synthase cDNA (SEQ ID NO:8) as a probe to screen a cDNA library prepared from wounded Grand fir (*Abies grandis*) sapling stems. A BLAST search identified the three geranyl diphosphate synthase cDNA molecules having the nucleic acid sequences set forth in SEQ ID NO:2 (called AgGPPS2), SEQ ID NO:4 (called AgGPPS1), and SEQ ID NO:6 (called AgGPPS3).

The portion of AgGPPS2 (SEQ ID NO:2) encoding the leader sequence was removed to produce the cDNA molecule having the sequence set forth in SEQ ID NO:9, which encodes the geranyl diphosphate synthase protein having the amino acid sequence set forth in SEQ ID NO:10. A cDNA molecule was also constructed from AgGPPS2 (SEQ ID NO:2) that lacked a leader sequence but included a series of 6 consecutive histidine residues at the C-terminus. The nucleic acid sequence of this cDNA molecule is set forth in SEQ ID NO:11, and encodes the geranyl diphosphate synthase protein having the amino acid sequence set forth in SEQ ID NO:12.

The portion of AgGPPS1 (SEQ ID NO:4) encoding the leader sequence was removed to produce the cDNA molecule having the sequence set forth in SEQ ID NO:13, which encodes the geranyl diphosphate synthase protein having the amino acid sequence set forth in SEQ ID NO:14. A cDNA molecule was also constructed from AgGPPS1 (SEQ ID NO:4) that lacked a leader sequence but included a series of 6 consecutive histidine residues at the C-terminus. The nucleic acid sequence of this cDNA molecule is set forth in SEQ ID NO:15, and encodes the geranyl diphosphate synthase protein having the amino acid sequence set forth in SEQ ID NO:16.

The portion of AgGPPS3 (SEQ ID NO:6) encoding the leader sequence was removed to produce the cDNA molecule having the sequence set forth in SEQ ID NO:17, which encodes the geranyl diphosphate synthase protein having the amino acid sequence set forth in SEQ ID NO:18. A cDNA molecule was also constructed from AgGPPS3 (SEQ ID NO:6) that lacked a leader sequence but included a series of 6 consecutive histidine residues at the C-terminus. The nucleic acid sequence of this cDNA molecule is set forth in SEQ ID NO:19, and encodes the geranyl diphosphate synthase protein having the amino acid sequence set forth in SEQ ID NO:20.

The His6-tagged geranyl diphosphate synthase proteins (SEQ ID NOS:12, 16, 20) were expressed in *E. coli*, and the expressed proteins purified and characterized. All of the expressed proteins (SEQ ID NOS:12, 16, 20) were able to catalyze the condensation of dimethylallyl diphosphate and isopentenyl diphosphate to form geranyl diphosphate.

Thus, in one aspect, the present invention provides isolated nucleic acid molecules that each encode a geranyl diphosphate synthase protein, wherein each isolated nucleic acid molecule hybridizes to a nucleic acid molecule consisting of the sequence set forth in SEQ ID NO:1 under conditions of 5×SSC at 45° C. for one hour. The nucleic acid sequence set forth in SEQ ID NO:1 is the complement of the nucleic acid sequence set forth in SEQ ID NO:2 that encodes a geranyl diphosphate synthase protein isolated from *A. grandis*.

Some isolated nucleic acid molecules of the invention encode a geranyl diphosphate synthase protein and hybridize to a nucleic acid molecule consisting of the sequence set forth in SEQ ID NO:1 under conditions of 5×SSC at 55° C. for one hour. Some isolated nucleic acid molecules of the invention encode a geranyl diphosphate synthase protein and hybridize to a nucleic acid molecule consisting of the sequence set forth in SEQ ID NO:1 under conditions of 5×SSC at 65° C. for one hour.

Hybridization can be conducted, for example, by utilizing the technique of hybridizing labeled nucleic acid probes to nucleic acid molecules immobilized on nitrocellulose filters or nylon membranes. An exemplary hybridization protocol is set forth in Example 2 herein. For example, utilizing the exemplary hybridization protocol set forth in Example 2, isolated nucleic acid molecules of the invention, that hybridize under conditions of 5×SSC at 45° C. for one hour to a nucleic acid molecule consisting of the sequence set forth in SEQ ID NO:1, can be identified by immobilizing a nucleic acid molecule consisting of the sequence set forth in SEQ ID NO:1 to a nylon membrane (or nitrocellulose filter). The membrane is incubated in aqueous solution in the presence of the probe nucleic acid molecule (such as an isolated nucleic acid molecule of the invention) under conditions of 5×SSC at 45° C. for 12 hours. The membrane is then washed under conditions of 5×SSC at 45° C. for one hour. An isolated nucleic acid molecule of the invention will remain hybridized to the immobilized target molecule under these wash conditions of 5×SSC at 45° C. for one hour.

In another aspect, the present invention provides isolated nucleic acid molecules that encode a geranyl diphosphate synthase protein, and that are each at least 70% identical to a nucleic acid molecule consisting of the nucleic acid sequence set forth in SEQ ID NO:9. Some isolated nucleic acid molecules of this aspect of the invention are at least 80% identical to a nucleic acid molecule consisting of the nucleic acid sequence set forth in SEQ ID NO:9. Some isolated nucleic acid molecules of this aspect of the invention are at least 90% identical to a nucleic acid molecule consisting of the nucleic acid sequence set forth in SEQ ID NO:9. Some isolated nucleic acid molecules of this aspect of the invention are at least 95% identical to a nucleic acid molecule consisting of the nucleic acid sequence set forth in SEQ ID NO:9. Some isolated nucleic acid molecules of this aspect of the invention are at least 99% identical to a nucleic acid molecule consisting of the nucleic acid sequence set forth in SEQ ID NO:9.

In another aspect, the present invention provides isolated nucleic acid molecules that encode a geranyl diphosphate synthase protein, and that are each at least 70% identical to a nucleic acid molecule consisting of the nucleic acid sequence set forth in SEQ ID NO:2. Some isolated nucleic acid molecules of this aspect of the invention are at least 80% identical to a nucleic acid molecule consisting of the nucleic acid sequence set forth in SEQ ID NO:2. Some isolated nucleic acid molecules of this aspect of the invention are at least 90% identical to a nucleic acid molecule consisting of the nucleic acid sequence set forth in SEQ ID NO:2. Some isolated nucleic acid molecules of this aspect of the invention are at least 95% identical to a nucleic acid molecule consisting of the nucleic acid sequence set forth in SEQ ID NO:2. Some isolated nucleic acid molecules of this aspect of the invention are at least 99% identical to a nucleic acid molecule consisting of the nucleic acid sequence set forth in SEQ ID NO:2.

Sequence identity is defined as the percentage of nucleic acid residues in a candidate nucleic acid sequence that are identical to the corresponding nucleic acid residues in a subject nucleic acid sequence (such as the nucleic acid sequence set forth in SEQ ID NO:2 or SEQ ID NO:9), after aligning the sequences to achieve the maximum percent identity. Nucleic acid sequence identity can be determined, for example, by using the alignment method of Needleman and Wunsch (*J. Mol. Biol.* 48:443-453 (1970)) which is incorporated into the GAP program, which is one of a suite of programs contained in the GCG package (Wisconsin Package Version 10.0, Genetics Computer Group (GCG), Madison, Wis.). GAP considers all possible alignments and gap positions between two sequences and creates a global alignment that maximizes the number of matched residues and minimizes the number and size of gaps. A scoring matrix is used to assign values for symbol matches. A gap creation penalty of fifty and a gap extension penalty of three are used to limit the insertion of gaps into the alignment.

The nucleic acid molecules of the invention can be isolated by using any useful cloning technique. For example, all, or one or more portions, of the complement of a nucleic acid molecule having a nucleic acid sequence set forth in SEQ ID NO:2, SEQ ID NO:4, or SEQ ID NO:6, can be used as a hybridization probe to screen a plant genomic, or cDNA, library. The technique of hybridizing radiolabeled nucleic acid probes to nucleic acids immobilized on nitrocellulose filters or nylon membranes can be used to screen the library. Exemplary hybridization and wash conditions for screening the genomic, or cDNA, library are: hybridization for 20 hours at 45° C. in 5.0×SSC, 0.5% sodium dodecyl sulfate, 1×Denhardt's solution; washing (three washes of twenty minutes each at 25° C.) in 2×SSC, 1% (w/v) sodium dodecyl sulfate, and one wash (for twenty minutes) in 5×SSC, 1% (w/v) sodium dodecyl sulfate, at 45° C. An optional further wash (for twenty minutes) can be conducted under conditions of 5×SSC, 1% (w/v) sodium dodecyl sulfate, at 55° C., or 65° C.

Again, by way of example, nucleic acid molecules of the invention can be isolated by the polymerase chain reaction (PCR) described in *The Polymerase Chain Reaction* (K. B. Mullis et al., eds. 1994). For example, Gobinda et al. (*PCR Methods Applic.* 2:318-22, 1993), incorporated herein by reference, disclose "restriction-site PCR" as a direct method which uses universal primers to retrieve unknown sequence adjacent to a known locus. First, genomic DNA is amplified in the presence of a linker-primer, that is homologous to a linker sequence ligated to the ends of the genomic DNA fragments, and in the presence of a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Further, by way of example, inverse PCR permits acquisition of unknown sequences starting with primers based on a known region (Triglia, T. et al., *Nucleic Acids Res* 16:8186, 1988). The method uses several restriction enzymes to generate a suitable fragment in the known region of a gene. The fragment is then circularized by intramolecular ligation and used as a PCR template. Divergent primers are designed from the known region. The nucleic acid molecules of the invention can also be synthesized using any method for synthesis of nucleic acid molecules.

In another aspect, the present invention provides vectors that each include a nucleic acid molecule that encodes a geranyl diphosphate synthase protein, wherein the nucleic acid molecule hybridizes to a nucleic acid molecule consisting of the sequence set forth in SEQ ID NO:1 under conditions of 5×SSC at 45° C. for one hour. Vectors that are functional in plants can be binary plasmids derived from *Agrobacterium* plasmids. Such vectors are capable of transforming plant cells. Briefly, these vectors typically contain left and right border sequences that are required for integration into the host (plant) chromosome. A nucleic acid molecule of the invention (encoding a geranyl diphosphate synthase protein) can be inserted between these border sequences. In some embodiments, a selectable marker gene is also included. The vector also may contain a bacterial origin of replication.

In another aspect, the present invention provides host cells including a vector of the invention. Host cells can be prokaryotic or eukaryotic, such as plant cells. Vectors of the invention can be introduced into plant cells using techniques well known to those skilled in the art. These methods include, but are not limited to, (1) direct DNA uptake, such as particle bombardment or electroporation (see, Klein et al., *Nature* 327:70-73, 1987; U.S. Pat. No. 4,945,050), and (2) *Agrobacterium*-mediated transformation (see, e.g., U.S. Pat. Nos. 6,051,757; 5,731,179; 4,693,976; 4,940,838; 5,464,763; and 5,149,645, each of which patents are incorporated herein by reference). Within the cell, the transgenic sequences may be incorporated within the chromosome.

Transgenic plants can be obtained, for example, by transferring vectors that include a selectable marker gene, (e.g., the kan gene encoding resistance to kanamycin), into *Agrobacterium tumifaciens* containing a helper Ti plasmid as described in Hoeckema et al., *Nature*, 303:179-181, 1983, and culturing the *Agrobacterium* cells with leaf slices, or other tissues or cells, of the plant to be transformed as described by An et al., *Plant Physiology*, 81:301-305, 1986.

Transformed plant calli may be selected through the selectable marker by growing the cells on a medium containing, for example, kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition to the methods described above, several methods are known in the art for transferring cloned DNA and vectors into a wide variety of plant species, including gymnosperms, angiosperms, monocots and dicots (see, e.g., Glick and Thompson, eds., *Methods in Plant Molecular Biology*, CRC Press, Boca Raton, Fla. (1993), incorporated by reference herein). Representative examples include electroporation-facilitated DNA uptake by protoplasts in which an electrical pulse transiently permeabilizes cell membranes, permitting the uptake of a variety of biological molecules, including recombinant DNA (see, e.g., Rhodes et al., *Science*, 240:204-207, 1988); treatment of protoplasts with polyethylene glycol (see, e.g., Lyznik et al., *Plant Molecular Biology*, 13:151-161, 1989); and bombardment of cells with DNA-laden microprojectiles which are propelled by explosive force or compressed gas to penetrate the cell wall (see, e.g., Klein et al., *Plant Physiol.* 91:440-444, 1989; and Boynton et al., *Science*, 240(4858):1534-1538, 1988). A method that has been applied to Rye plants (*Secale cereale*) is to directly inject plasmid DNA, including a selectable marker gene, into developing floral tillers (de la Pena et al., *Nature* 325:274-276, 1987). Further, plant viruses can be used as vectors to transfer genes to plant cells. Examples of plant viruses that can be used as vectors to transform plants include the Cauliflower Mosaic Virus (see, e.g., Brisson et al., *Nature* 310:511-514, 1984). Other useful techniques include: site-specific recombination using the Cre-lox system (see, U.S. Pat. No. 5,635,381); and insertion into a target sequence by homologous recombination (see, U.S. Pat. No. 5,501,967). Additionally, plant transformation strategies and techniques are reviewed in Birch, R. G., *Ann. Rev. Plant Phys. Plant Mol. Biol.*, 48:297, 1997; and Forester et al., *Exp. Agric.*, 33:15-33, 1997.

Positive selection markers may also be utilized to identify plant cells that include a vector of the invention. For example, U.S. Pat. Nos. 5,994,629, 5,767,378, and 5,599,670, describe the use of a β-glucuronidase transgene and application of cytokinin-glucuronide for selection, and use of mannophosphatase or phosphmanno-isomerase transgene and application of mannose for selection.

The cells which have been transformed may be grown into plants by a variety of art-recognized means. See, for example, McConnick et al., *Plant Cell Reports* 5:81-84 (1986). These plants may then be grown, and either selfed or crossed with a different plant strain, and the resulting homozygotes or hybrids having the desired phenotypic characteristic (e.g., expression of elevated levels of geranyl diphosphate synthase) identified. Two or more generations may be grown to ensure that the subject phenotypic characteristic is stably maintained and inherited and then seeds harvested to ensure the desired phenotype or other property has been achieved.

The following are representative plant species into which a vector of the invention may be introduced. The citations are to representative publications disclosing genetic transformation protocols that can be used to genetically transform the listed plant species. Rice (Alam, M. F. et al., *Plant Cell Rep.* 18:572-575, 1999); maize (U.S. Pat. Nos. 5,177,010 and 5,981,840); wheat (Ortiz, J. P. A., et al., *Plant Cell Rep.* 15:877-881, 1996); tomato (U.S. Pat. No. 5,159,135); potato (Kumar, A., et al., *Plant J.* 9:821-829, 1996); cassaya (Li, H.-Q., et al., *Nat. Biotechnology* 14:736-740, 1996); lettuce (Michelmore, R., et al., *Plant Cell Rep.* 6:439-442, 1987); tobacco (Horsch, R. B., et al., *Science* 227:1229-1231, 1985); cotton (U.S. Pat. Nos. 5,846,797 and 5,004,863); grasses (U.S. Pat. Nos. 5,187,073 and 6,020,539); peppermint (X. Niu et al., *Plant Cell Rep.* 17:165-171, 1998); citrus plants (Pena, L. et al., *Plant Sci.* 104:183-191, 1995); caraway (F. A. Krens, et al., *Plant Cell Rep.* 17:39-43, 1997); banana (U.S. Pat. No. 5,792,935); soybean (U.S. Pat. Nos. 5,416,011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); and cereals (U.S. Pat. No. 6,074,877). Representative transformation protocols for *Picea* species are set forth in D. H. Clapham et al., *Molecular Biology of Woody Plants* (S. M. Jain and S. C. Minocha, eds.) Vol. 2, 105-118 (2000), Kluwer Academic Publishers.

Cultures of mammalian host cells, and other host cells that do not have rigid cell membrane barriers, can be transformed, for example, using the calcium phosphate method as originally described by Graham and Van der Eb (*Virology*, 52:546, 1978) and modified as described in sections 16.32-16.37 of Sambrook et al., supra. However, other methods for introducing DNA into cells, such as Polybrene (Kawai and Nishizawa, *Mol. Cell. Biol.*, 4:1172, 1984), protoplast fusion (Schaffner, *Proc. Natl. Acad. Sci. USA*, 77:2163, 1980), electroporation (Neumann et al., *EMBO J.*, 1:841, 1982), and direct microinjection into nuclei (Capecchi, *Cell*, 22:479, 1980), may also be used. Additionally, animal transformation strategies are reviewed in Monastersky, G. M., and Robl, J. M., *Strategies in Transgenic Animal Science*, ASM Press, Washington, D.C., 1995.

Prokaryotic host cells can be transformed, for example, using the calcium chloride method as described in section 1.82 of Sambrook et al., supra. Electroporation may also be used for transformation of these cells. Representative prokaryote transformation techniques are set forth in Dower, W. J., in *Genetic Engineering, Principles and Methods*, 12:275-296, Plenum Publishing Corp., 1990; Hanahan et al., *Meth. Enzymol.*, 204:63, 1991.

In another aspect, the present invention provides cultured plant tissue (e.g., plant tissue from a plant of the genus *Abies*) comprising a vector comprising a nucleic acid molecule that encodes a geranyl diphosphate synthase protein, wherein the nucleic acid molecule hybridizes to a nucleic acid molecule consisting of the sequence set forth in SEQ ID NO:1 under conditions of 5×SSC at 45° C. for one hour. For example, an expression vector of the invention can be introduced into one, or more, plant cells using any of the techniques described herein for introducing nucleic acid molecules into plant cells. The plant cells can then be cultured to produce cultured plant tissue. Representative, art-recognized, methods for culturing plant tissue are described, for example, in O. L. Gamborg and G. C. Phillips (Eds.) Plant Cell, Tissue and Organ Culture: Fundamental Methods, Springer Verlag, Berlin, 1995; and in R. D. Hall (Ed.) Plant Cell Culture Protocols, Humana Press, Totowa, N.J., 1999.

In another aspect, the present invention provides methods for increasing the level of geranyl diphosphate synthase in a living cell, wherein the methods each include the step of introducing into a living cell an expression vector comprising a nucleic acid molecule that encodes a geranyl diphosphate synthase protein under conditions that enable expression of the geranyl diphosphate synthase protein, wherein the nucleic acid molecule hybridizes to a nucleic acid molecule consisting of the sequence set forth in SEQ ID NO:1 under conditions of 5×SSC at 45° C. for one hour. In the practice of some embodiments of the methods of this aspect of the invention, the nucleic acid molecule that encodes a geranyl diphosphate synthase hybridizes to a nucleic acid molecule consisting of the sequence set forth in SEQ ID NO:1 under conditions of 5×SSC at 55° C. for one hour. In the practice of some embodiments of the methods of this aspect of the invention, the nucleic acid molecule that encodes a geranyl diphosphate synthase protein hybridizes to a nucleic acid molecule consisting of the sequence set forth in SEQ ID NO:1 under conditions of 5×SSC at 65° C. for one hour.

In another aspect, the present invention provides methods for decreasing the level of geranyl diphosphate synthase in a living cell, the methods of this aspect of the invention each include the step of introducing into a living cell an expression vector comprising a nucleic acid molecule that hybridizes to a nucleic acid molecule consisting of the sequence set forth in SEQ ID NO:2, under conditions of 5×SSC at 45° C. for one hour, under conditions that enable expression of the introduced nucleic acid molecule. In the practice of some embodiments of the methods of this aspect of the invention, the nucleic acid molecule hybridizes to a nucleic acid molecule consisting of the sequence set forth in SEQ ID NO:2 under conditions of 5×SSC at 55° C. for one hour. In the practice of some embodiments of the methods of this aspect of the invention, the nucleic acid molecule hybridizes to a nucleic acid molecule consisting of the sequence set forth in SEQ ID NO:2 under conditions of 5×SSC at 65° C. for one hour. While not wishing to be bound by theory, it is believed that the expressed nucleic acid molecule interacts (e.g., by Watson-Crick base pairing) with a gene, or mRNA molecules, encoding geranyl diphosphate synthase within the cell, thereby reducing or eliminating the expression of geranyl diphosphate synthase.

In the practice of the methods of the invention for increasing, or decreasing, the level of geranyl diphosphate synthase in a living cell (e.g., a plant cell), an expression vector can be introduced into a living cell by any useful means, such as any of the representative techniques described supra. An expression vector of the present invention can be introduced into one, or more, individual living cells, and whole organisms (e.g., plants) may be regenerated therefrom to yield organisms in which the level of geranyl diphosphate synthase is increased or decreased.

In another aspect, the present invention provides isolated geranyl diphosphate synthase proteins that are each at least 70% identical to the geranyl diphosphate synthase protein having the amino acid sequence set forth in SEQ ID NO:10. The protein having the amino acid sequence set forth in SEQ ID NO:10 is the mature version of the protein having the amino acid sequence set forth in SEQ ID NO:3, but lacking the leader sequence extending from residues 1 through 86 of SEQ ID NO:3. The leader sequence directs the geranyl diphosphate synthase protein to a membrane-bound compartment within a living cell and is cleaved from the geranyl diphosphate synthase protein within the living cell. The amino acid sequence characteristics of leader sequences are described, for example, by G. von Heijne et al., *Eur. J. Biochem*. 180:535-545, 1989.

Some isolated proteins of this aspect of the invention are at least 80% identical to the geranyl diphosphate synthase protein having the amino acid sequence set forth in SEQ ID NO:10. Some isolated proteins of this aspect of the invention are at least 90% identical to the geranyl diphosphate synthase protein having the amino acid sequence set forth in SEQ ID NO:10. Some isolated proteins of this aspect of the invention are at least 95% identical to the geranyl diphosphate synthase protein having the amino acid sequence set forth in SEQ ID NO:10. Some isolated proteins of this aspect of the invention are at least 99% identical to the geranyl diphosphate synthase protein having the amino acid sequence set forth in SEQ ID NO:10.

Representative examples of isolated proteins of this aspect of the invention include the proteins having the amino acid sequences set forth in SEQ ID NO:10, SEQ ID NO:14 and SEQ ID NO:18. The protein having the amino acid sequence set forth in SEQ ID NO:14 is the mature version of the protein having the amino acid sequence set forth in SEQ ID NO:5, but lacking the leader sequence extending from residues 1 through 86 of SEQ ID NO:5. The protein having the amino acid sequence set forth in SEQ ID NO:18 is the mature version of the protein having the amino acid sequence set forth in SEQ ID NO:7, but lacking the leader sequence extending from residues 1 through 92 of SEQ ID NO:7.

In a related aspect, the present invention provides isolated geranyl diphosphate synthase proteins that are each at least 70% identical to the geranyl diphosphate synthase protein having the amino acid sequence set forth in SEQ ID NO:3. Some isolated proteins of this aspect of the invention are at least 80% identical to the geranyl diphosphate synthase protein having the amino acid sequence set forth in SEQ ID NO:3. Some isolated proteins of this aspect of the invention are at least 90% identical to the geranyl diphosphate synthase protein having the amino acid sequence set forth in SEQ ID NO:3. Some isolated proteins of this aspect of the invention are at least 95% identical to the geranyl diphosphate synthase protein having the amino acid sequence set forth in SEQ ID NO:3. Some isolated proteins of this aspect of the invention are at least 99% identical to the geranyl diphosphate synthase protein having the amino acid sequence set forth in SEQ ID NO:3. Representative examples of isolated proteins of this aspect of the invention include the proteins having the amino acid sequences set forth in SEQ ID NO:3, SEQ ID NO:5 and SEQ ID NO:7.

The term "percent identity" or "percent identical" when used in connection with the proteins of the present invention, is defined as the percentage of amino acid residues in a candidate protein that are identical with a subject protein (such as the amino acid sequence of SEQ ID NO:3), after aligning the candidate and subject sequences to achieve the maximum percent identity. Amino acid sequence identity can be determined, for example, by using the alignment method of Needleman and Wunsch (*J. Mol. Biol*. 48:443-453 (1970)) which is incorporated into the GAP program, as described supra. A gap creation penalty of fifty and a gap extension penalty of three are used to limit the insertion of gaps into the alignment.

It is understood that the isolated geranyl diphosphate synthase proteins of the invention include, for example, geranyl diphosphate synthase proteins isolated from organisms (e.g., from plants) that normally express a geranyl diphosphate synthase, and geranyl diphosphate synthase proteins isolated from organisms (e.g., microorganisms) that do not normally express a geranyl diphosphate synthase. The nucleic acid molecule (e.g., cDNA molecule) within an organism that encodes and expresses a geranyl diphosphate synthase protein may be, for example, artificial (e.g., synthesized by artificial means in a laboratory), or may be, for example, a mutagenized, or otherwise altered, variant of a naturally-occurring nucleic acid molecule that encodes a geranyl diphosphate synthase protein.

Proteins of the invention can be isolated, for example, by expressing nucleic acid molecules encoding the desired protein (e.g., geranyl diphosphate synthase protein) in a suitable host cell, such as *E. coli*. By way of representative example, a nucleic acid molecule (such as a cDNA molecule) encoding a protein of the invention is cloned into a plasmid vector, such as a Bluescript plasmid (available from Stratagene, Inc., La Jolla, Calif.). The recombinant vector is then introduced into an *E. coli* strain (such as *E. coli* XL1-Blue, also available from Stratagene, Inc.) and the protein encoded by the nucleic acid molecule is expressed in *E. coli* and then purified. For example, *E. coli* XL1-Blue harboring a Bluescript vector including a cDNA molecule of interest is grown overnight at 37° C. in LB medium containing 100 µg ampicillin/ml. A 50 µl aliquot of the overnight culture is used to inoculate 5 ml of fresh LB medium containing ampicillin, and the culture grown at 37° C. with vigorous agitation to $A_{600}$=0.5 before induction with 1 mM IPTG. After an additional two hours of growth, the suspension is centrifuged (1000×g, 15 min, 4° C.), the media removed, and the pelleted cells resuspended in 1 ml of cold buffer that preferably contains 1 mM EDTA and one or more proteinase inhibitors. The cells can be disrupted by sonication with a microprobe. The chilled sonicate is cleared by centrifugation and the expressed, recombinant polypeptide purified from the supernatant by art-recognized protein purification techniques, such as those described herein.

Representative examples of art-recognized techniques for purifying, or partially purifying, proteins from biological material, such as from prokaryotic cells that express the desired protein(s), are: exclusion chromatography, ion-exchange chromatography, hydrophobic interaction chromatography, reversed-phase chromatography and immobilized metal affinity chromatography.

Hydrophobic interaction chromatography and reversed-phase chromatography are two separation methods based on the interactions between the hydrophobic moieties of a sample and an insoluble, immobilized hydrophobic group present on the chromatography matrix. In hydrophobic interaction chromatography the matrix is hydrophilic and is substituted with short-chain phenyl or octyl nonpolar groups. The mobile phase is usually an aqueous salt solution. In reversed phase chromatography the matrix is silica that has been substituted with longer n-alkyl chains, usually $C_8$ (octylsilyl) or $C_{18}$ (octadecylsilyl). The matrix is less polar than the mobile phase. The mobile phase is usually a mixture of water and a less polar organic modifier.

Separations on hydrophobic interaction chromatography matrices are usually done in aqueous salt solutions, which generally are nondenaturing conditions. Samples are loaded onto the matrix in a high-salt buffer and elution is by a descending salt gradient. Separations on reversed-phase media are usually done in mixtures of aqueous and organic solvents, which are often denaturing conditions. In the case of polypeptide and/or peptide purification, hydrophobic interaction chromatography depends on surface hydrophobic groups and is carried out under conditions which maintain the integrity of the polypeptide molecule. Reversed-phase chromatography depends on the native hydrophobicity of the protein and is carried out under conditions which expose nearly all hydrophobic groups to the matrix, i.e., denaturing conditions.

Ion-exchange chromatography is designed specifically for the separation of ionic or ionizable compounds. The stationary phase (column matrix material) carries ionizable functional groups, fixed by chemical bonding to the stationary phase. These fixed charges carry a counterion of opposite sign. This counterion is not fixed and can be displaced. Ion-exchange chromatography is named on the basis of the sign of the displaceable charges. Thus, in anion ion-exchange chromatography the fixed charges are positive and in cation ion-exchange chromatography the fixed charges are negative.

Retention of a molecule on an ion-exchange chromatography column involves an electrostatic interaction between the fixed charges and those of the molecule, binding involves replacement of the nonfixed ions by the molecule. Elution, in turn, involves displacement of the molecule from the fixed charges by a new counterion with a greater affinity for the fixed charges than the molecule, and which then becomes the new, nonfixed ion.

The ability of counterions (salts) to displace molecules bound to fixed charges is a function of the difference in affinities between the fixed charges and the nonfixed charges of both the molecule and the salt. Affinities in turn are affected by several variables, including the magnitude of the net charge of the molecule and the concentration and type of salt used for displacement.

Solid-phase packings used in ion-exchange chromatography include cellulose, dextrans, agarose, and polystyrene. The exchange groups used include DEAE (diethylaminoethyl), a weak base, that will have a net positive charge when ionized and will therefore bind and exchange anions; and CM (carboxymethyl), a weak acid, with a negative charge when ionized that will bind and exchange cations. Another form of weak anion exchanger contains the PEI (polyethyleneimine) functional group. This material, most usually found on thin layer sheets, is useful for binding proteins at pH values above their pI. The polystyrene matrix can be obtained with quaternary ammonium functional groups for strong base anion exchange or with sulfonic acid functional groups for strong acid cation exchange. Intermediate and weak ion-exchange materials are also available. Ion-exchange chromatography need not be performed using a column, and can be performed as batch ion-exchange chromatography with the slurry of the stationary phase in a vessel such as a beaker.

Gel filtration is performed using porous beads as the chromatographic support. A column constructed from such beads will have two measurable liquid volumes, the external volume, consisting of the liquid between the beads, and the internal volume, consisting of the liquid within the pores of the beads. Large molecules will equilibrate only with the external volume while small molecules will equilibrate with both the external and internal volumes. A mixture of molecules (such as proteins) is applied in a discrete volume or zone at the top of a gel filtration column and allowed to percolate through the column. The large molecules are excluded from the internal volume and therefore emerge first from the column while the smaller molecules, which can access the internal volume, emerge later. The volume of a conventional matrix used for protein purification is typically 30 to 100 times the volume of the sample to be fractionated. The absorbance of the column effluent can be continuously monitored at a desired wavelength using a flow monitor.

A technique that is often applied to the purification of proteins is High Performance Liquid Chromatography (HPLC). HPLC is an advancement in both the operational theory and fabrication of traditional chromatographic systems. HPLC systems for the separation of biological macromolecules vary from the traditional column chromatographic systems in three ways; (1) the column packing materials are of much greater mechanical strength, (2) the particle size of the column packing materials has been decreased 5- to 10-fold to enhance adsorption-desorption kinetics and diminish bandspreading, and (3) the columns are operated at 10-60 times higher mobile-phase velocity. Thus, by way of non-limiting example, HPLC can utilize exclusion chromatography, ion-exchange chromatography, hydrophobic interaction chromatography, reversed-phase chromatography and immobilized metal affinity chromatography. Art-recognized techniques for the purification of proteins and peptides are set forth in *Methods in Enzymology, Vol. 182, Guide to Protein Purification*, Murray P. Deutscher, ed. (1990).

The following examples merely illustrate the best mode now contemplated for practicing the invention, but should not be construed to limit the invention. All literature citations herein are expressly incorporated by reference.

EXAMPLE 1

This Example describes the isolation of three cDNA molecules (SEQ ID NO:2, SEQ ID NO:4, and SEQ ID NO:6) encoding geranyl diphosphate synthase from Grand fir (*Abies grandis*).

Substrates reagents and cDNA library. [4-$^{14}$C]IPP (54 Ci/mol) was purchased from DuPont/NEN. Unlabeled IPP, DMAPP, GPP, and FPP were purchased from Echelon Research Laboratories (Salt Lake City, Utah). Authentic terpenol standards were from the inventors' own collection. Synthesis of oligonucleotide primers was performed by GIBCO BRL. Alkaline phosphatase, apyrase, and protein molecular weight standards were purchased from Sigma. Construction of the λZAP II cDNA library, using mRNA isolated from wounded grand fir sapling stems (E. Lewinsohn et al., *Plant Mol. Biol. Rep.* 12:20-25, 1994) was described previously (B. S. Vogel et al., *J. Biol. Chem.* 271:23262-23268, 1996).

Probe construction and library screening. Standard PCR protocols (J. Sambrook et al., *Molecular Cloning: A Laboratory Manual*, 2nd ed., Cold Spring Harbor Laboratory Press, Cold Spring Harbor, N.Y., 1989) were employed to amplify a 5'-truncated version of the *Taxus canadensis* GGPP synthase (E98M) (SEQ ID NO:8) using template and primers previously described (C. Burke and R. Croteau, *J. Biol. Chem.* 277:3141-3149, 2002). The resulting gel-purified amplicon (SEQ ID NO:8) was labeled with [α-$^{32}$P]CTP by the random hexamer method (J. Sambrook et al., *Molecular Cloning: A Laboratory Manual*, 2nd ed., Cold Spring Harbor Laboratory Press, Cold Spring Harbor, N.Y., 1989) and used as a hybridization probe to screen transfer membranes (Hybond-N; Amersham Biosciences) containing $1.8 \times 10^5$ plaques from the grand fir cDNA library plated on *E. coli* XL1-blue cells (Stratagene). Hybridization was performed at 47° C. for 18 h in Rapid-hyb Buffer (Amersham Biosciences). Membranes were washed in 5×SSC solution for 10 min at 20° C. followed by 15 min. in 2.5×SSC solution at 47° C., and were then exposed to imaging film (X-OMAT; Kodak) for 2 days. Positive plaques were re-plated and screened with the hybridization probe (SEQ ID NO:8) two additional times. Purified λZAP II clones were excised in vivo as pBluescript phagemids and transformed into *E. coli* SOLR cells following the manufacturer's protocol (Stratagene).

Generation of *E. coli* expression constructs. A BLAST search (S. F. Altschul et al., *J. Mol. Biol.* 215:403-410, 1990) using sequence data (DyeDeoxy Terminator Cycle Sequencing, Applied Biosystems) obtained from each positive clone derived from the hybridization screen revealed that nine of eleven clones tested contained sequences homologous to the *Taxus canadensis* GGPP synthase (70-78% identity). Further analysis indicated that four unique full-length sequences (designated AgGPPS1 (SEQ ID NO:4), AgGPPS2 (SEQ ID NO:2) and AgGPPS3 (SEQ ID NO:6) and AgGGPPS (SEQ ID NO:21, encoding the protein having the amino acid sequence set forth in SEQ ID NO:22)) were represented in the set. Full-length and N-terminally truncated (targeting peptide deleted) versions of each sequence were amplified (with and without a C-terminal His6 tag) by PCR, and were sub-cloned into the pET32a expression vector (Novagen). Thus. the nucleic acid sequences of the full-length cDNA molecules are set forth in SEQ ID NO:4 (AgGPPS1), SEQ ID NO:2 (AgGPPS2), SEQ ID NO:6 (AgGPPS3) and SEQ ID NO:21 (AgGGPPS). The nucleic acid sequences of the cDNA molecules encoding the N-terminally-truncated synthases (without a C-terminal His6 tag) are set forth in SEQ ID NO:9 (encoding AgGPPS2 truncated protein (SEQ ID NO:10)), SEQ ID NO:13 (encoding AgGPPS1 truncated protein (SEQ ID NO:14)), SEQ ID NO:17 (encoding AgGPPS3 truncated protein (SEQ ID NO:18)), and SEQ ID NO:23 (encoding AgGGPPS truncated protein (SEQ ID NO:24)). The nucleic acid sequences of the cDNA molecules encoding the N-terminally-truncated synthases (with a C-terminal His6 tag) are set forth in SEQ ID NO:11 (encoding AgGPPS2 truncated protein (SEQ ID NO:12)), SEQ ID NO:15 (encoding AgGPPS1 truncated protein (SEQ ID NO:16)), SEQ ID NO:19 (encoding AgGPPS3 truncated protein (SEQ ID NO:20)), and SEQ ID NO:25 (encoding AgGGPPS truncated protein (SEQ ID NO:26)).

Full-length and truncated versions of AgGPPS1 (SEQ ID NO:4) were generated using forward primers 5'-GAA ATA GAA CAA ACA TAT GGC TTA CAG TTG-3' (full-length) (SEQ ID NO:27) and 5'-GGA AAA GGC CCA TAT GTT TGA TTT CAA GG-3' (SEQ ID NO:28) (for the truncated E88M mutation) and reverse primers 5'-GAA CAC ATT TCT CGA GCT TTT CAG TTC-3' (SEQ ID NO:29) (no His6 tag) and 5'-CAT TTC GCA GGC CTC GAG GTT CTG TCT TAA TG-3' (SEQ ID NO:30) (with His6 tag). Full-length and truncated versions of AgGPPS2 (SEQ ID NO:2) were generated using forward primers 5'-CTA ATC ATA TAA AGA GCA TAT GGC TTA CAG TGC-3' (SEQ ID NO:31) (full-length) and 5'-GGA AGA AGG CCC ATA TGT TTG ATT TC-3' (SEQ ID NO:32) (for the truncated E86M mutation) and reverse primers 5'-CAA ACA AGA ACG CTC GAG GAG GCT CTT C-3' (SEQ ID NO:33) (no His6 tag) and 5'-GCT TTG AGG AGG CTC GAG ATT TTG TCT G-3' (SEQ ID NO:34) (with His6 tag).

Full-length and truncated versions of AgGPPS3 (SEQ ID NO:6) were generated using forward primers 5'-GGC TTA CAG TCA TAT GGT ACG TAG C-3' (SEQ ID NO:35) (full-length) and 5'-GGA AGA AGG TCC ATA TGT TTG ATT TC-3' (SEQ ID NO:36) (for the truncated E92M mutation) and reverse primers 5'-GGA ACG ATT TTA CTC GAG TTT TCA ATT C-3' (SEQ ID NO:37) (no His6 tag) and 5'-GGA ACG ATT TTA CTC GAG TTT TCA ATT C-3' (SEQ ID NO:38) (with His6 tag). Full-length and truncated versions of AgGGPPPS (SEQ ID NO:21) were generated using forward primers 5'-GAA ATA GAA CAA ACA TAT GGC TTA TAG C-3' (SEQ ID NO:39) (full-length) and 5'-GGA GAA GGT CCA TAT GTT TGA CTT CAA GG-3' (SEQ ID NO:40) (for the truncated E88M mutation) and reverse primers 5'-CAT AAG AAC ACT TCT CGA GGC TCT TCA GTT TTG-3' (no His6 tag)(SEQ ID NO:41) and 5'-CAC TTT TAG AGG CTC GAG GTT TTG TCT G-3' (with His6 tag)(SEQ ID NO:42).

An Nde1 restriction site was created at the starting methionine, and a Xho1 restriction site was introduced beyond the stop codon. In the case of histidine tagged species (SEQ ID NOS:11, 15, 19, 25), the stop codon was mutated to a leucine codon to permit read through of the histidine tag included in the pET32a vector.

All pET32a constructs were transformed into *E. coli* BL21-CodonPlus (DE3)-RIL cells (Stratagene) for protein expression under conditions previously reported (C. Burke and R. Croteau, *J. Biol. Chem.* 277:3141-3149, 2002), except that Luria-Bertani medium (J. Sambrook et al., *Molecular Cloning: A Laboratory Manual*, 2nd ed., Cold Spring Harbor Laboratory Press, Cold Spring Harbor, N.Y., 1989) was replaced by sorbitol-betaine medium (J. R. Blackwell and R. Horgan, *FEBS Lett.* 295:10-12, 1991) to improve production of the soluble protein.

Protein purification and product determination. The affinity-based purification procedure for His-tagged proteins has been described previously, as has the standard purification protocol for the corresponding non-tagged proteins (C. Burke and R. Croteau, *J. Biol. Chem.*277:3141-3149, 2002). The partial purification procedure for the native GPP synthase from *A. grandis* has also been reported previously (D. Tholl et al., *Arch. Biochem. Biophys.* 386:233-242, 2001). Procedures for polyclonal antibody preparation were as described previously (C. C. Burke et al., *Proc. Natl. Acad. Sci. USA* 96:13062-13067, 1999), in this case using the SDS-PAGE purified AgGPPS3 protein (SEQ ID NO:7) as antigen. The assay procedures and methods for product analysis were similar to those previously described (C. Burke and R. Croteau, *J. Biol. Chem.* 277:3141-3149, 2002), except that for radio-GC a Raga (Raytest) radio-detector connected in-line to a Series 600 (Gow-Mac) chromatograph was employed with a 5% phenyl polysiloxane (ZB-5; Phenomenex) capillary column under hydrogen gas flow (70° C. for 5 min. followed by an 8° C. per min. ramp to 240° C. for 5 min).

Molecular weight determination and kinetic evaluation. The molecular weight of GPP synthase was determined by gel filtration chromatography on a calibrated XK 16/70 column of Superdex 200 (Amersham Biosciences) as previously described (C. Burke and R. Croteau, *J. Biol. Chem.* 277:3141-3149, 2002). For kinetic evaluation, the standard prenyltransferase assay was performed (C. Burke and R. Croteau, *J. Biol. Chem.* 277:3141-3149, 2002) but the reaction was terminated after 4 min. to ensure linearity in the rate measurements. For preparative incubations, the reaction time was extended to 8 min., and all assays contained from 0.25 to 1.0 µg of purified protein.

Isolation of geranyl diphosphate synthase clones. Wound-induced stem tissue of grand fir (*Abies grandis*) produces abundant monoterpenes in the secreted oleoresin (E. Lewinsohn et al., *Plant Physiol.* 96:44-49, 1991) and contains substantial GPP synthase activity (D. Tholl et al., *Arch. Biochem. Biophys.* 386:233-242, 2001). Plaque hybridization with a *Mentha* small subunit GPP synthase probe yielded no sequences with similarity to prenyltransferases; however, hybridization with a *Taxus* GGPP synthase probe (SEQ ID NO:8) yielded nine purified clones encoding sequences with substantial deduced identity (>60% Identity) to the *Taxus* GGPP synthase. Comparison of these sequences indicated that four unique full-length clones (SEQ ID NOS:2,4,6 and 21) had been discovered that bore deduced amino acid sequence identities of 66% to 73% relative to the *Taxus* GGPP synthase. The deduced amino acid sequences of these presumptive prenyltransferases encode proteins of 41.3 to 42.4 kDa, and contain the two aspartate-rich motifs that are characteristic of this enzyme type (P. F. Marrero et al., *J. Biol. Chem.* 267:21873-21878, 1992; L. Song and C. D. Poulter, *Proc. Natl. Acad. Sci. USA* 91:3044-3048, 1994), including the GPP synthase large subunit of *Mentha* (C. C. Burke et al., *Proc. Natl. Acad. Sci. USA* 96:13062-13067, 1999).

Functional expression of GGPP synthase and GPP synthase. To determine the function of each clone, each cDNA (SEQ ID NOS:2,4,6 and 21) was subcloned into pET32a and transformed into *E. coli* BL21-CodonPlus (DE3)-RIL cells for expression. Because prior studies with GPP synthase and GGPP synthase indicated that optimal expression of the soluble recombinant enzyme was obtained after deleting the N-terminal plastidial targeting sequence (C. Burke and R. Croteau, *J. Biol. Chem.* 277:3141-3149, 2002), expression from plasmids containing both full-length (SEQ ID NOS:2, 4,6 and 21) and truncated (SEQ ID NOS:9, 13, 17 and 23) versions of each sequence was evaluated. Because it was also previously demonstrated that C-terminal His8 tagging of the *Mentha* GPP synthase provided an effective means of purification without apparent effect on catalysis or product formation (C. Burke and R. Croteau, *J. Biol. Chem.* 277:3141-3149, 2002), the similarly (His6) tagged, truncated versions (SEQ ID NOS:11, 15, 19 and 25) were also generated and evaluated.

Truncation sites were selected based upon Pileup comparison (Genetics Computer Group, Program Manual for the Wisconsin Package, Ver. 10, Madison, Wis., 1998) between these sequences and those of GPP synthase and other plant GGPP synthases. Because GPP synthases and GGPP synthases of plant origin are localized to plastids (F. Bouvier et al., *Plant J.* 24:241-252, 2000; E. Soler et al., *Planta* 187: 171-175, 1992; W. Sitthithawom et al., *Chem. Pharm. Bull.* 49:197-202, 2001; K. Okada et al., *Plant Physiol.* 122:1045-1056, 2000), they are translated as preproteins bearing cleavable N-terminal targeting sequences (K. Keegstra et al., *Physiol. Plant.* 93:157-162, 1995) that tend to be quite variable (G. von Heijne et al., *Eur. J. Biochem.* 180:535-545, 1989). Thus, the truncation sites were selected at a point in the sequences where a high level of amino acid conservation is initiated, such that the truncated species (SEQ ID NOS:9, 13, 17 and 23) more closely resemble the mature forms of these enzymes.

As might be expected based on prior experience, the full-length (preprotein) versions of these enzymes (SEQ ID NOS: 3, 5, 7 and 22) were not efficiently expressed in soluble form and the bulk of the protein generated was in inclusion bodies. However, the truncated versions of these enzymes with the appended C-terminal His6-tag (SEQ ID NOS:12, 16, 20 and 26) readily afforded soluble protein that was affinity purified to >90% in amounts up to 6 mg/L. To define the function of these presumptive prenyltransferases, assays were conducted with the purified proteins (SEQ ID NOS:12, 16, 20 and 26) using [4-$^{14}$C]IPP and DMAPP as co-substrates and MgCl$_2$ as cofactor. The resulting products were enzymatically hydrolyzed to the corresponding alcohols and analyzed by radio-GC. His-tagged GGPPS (SEQ ID NO:26) yielded predominately geranylgeranyl diphosphate as product with trace amounts of geranyl diphosphate, indicating that this acquisition was a bona fide GGPP synthase as expected based on the sequence. His-tagged AgGPPS1 (SEQ ID NO:16), AgGPPS2 (SEQ ID NO:12) and AgGPPS3 (SEQ ID NO:20) all yielded geranyl diphosphate as the major product under these assay conditions, and the His-tagged AgGPPS3 enzyme (SEQ ID NO:20) also produced about 30% farnesyl diphosphate. His-tagged AgGPPS1 (SEQ ID NO:16) and AgGPPS3 (SEQ ID NO:20) were able to accept GPP as the allylic co-substrate (110% the rate with DMAPP under standard assay conditions) in the production of FPP, and His-tagged AgGPPS3 (SEQ ID NO:20) could also efficiently utilize FPP as allylic co-substrate in the formation of GGPP (at about 50% the rate with DMAPP as co-substrate). However, His-tagged AgGPPS2 (SEQ ID NO:12) could utilize only DMAPP as co-substrate and yielded only GPP as product, indicating that His-tagged AgGPPS2 (SEQ ID NO:12) was the most selective in substrate use and the most specific in chain length production of the three isoforms. Assays with the full-length versions (SEQ ID NOS:3, 5 and 7) and untagged versions (SEQ ID NOS:10, 14 and 18) of these GPP synthases demonstrated that neither the N-terminal transit peptide nor the C-terminal tag had influence on the selectivities or product distributions of these enzymes.

Sequence comparisons between the three GPP synthases from grand fir (SEQ ID NOS:3, 5 and 7) and the GGPP synthase from this species (SEQ ID NO:22), at the level of deduced amino acid identity, indicated a range of 69-81% identity for the preproteins (SEQ ID NOS:3, 5, 7 and 22) and a range of 76-84% identity for the corresponding truncated species (SEQ ID NOS:10, 14, 18 and 24). The GPP synthase from *Arabidopsis* (F. Bouvier et al., *Plant J.* 24:241-252, 2000) exhibits deduced sequence identities for the full-length form of only 25% to 29% when compared to the three grand fir GPP synthases (SEQ ID NOS:3, 5 and 7).

Subunit architecture of GPP synthases from grand fir. To determine the subunit architecture of the recombinant grand fir GPP synthases (SEQ ID NOS:12, 16, and 20), each purified enzyme was separated on a calibrated Superdex 200 column. The size determined for all three GPP synthase isoforms (SEQ ID NOS:12, 16, and 20) (containing the C-terminal tag) was 64±4 kDa, which is consistent with a homodimeric structure (i.e., calculated subunit size of 33 kDa from the corresponding cDNA). Comparative immunoblotting, employing polyclonal antibodies that recognize AgGPPS1-3 (SEQ ID NOS:3, 5 and 7), clearly demonstrated the presence of a 27 kDa protein corresponding to the native GPP synthase in partially purified grand fir stem tissue extracts. Thus, the native synthase was approximately 5 kDa smaller than the truncated recombinant versions (SEQ ID NOS:12, 16, and 20) of the enzyme prepared in this study, indicating a more interior proteolytic cleavage site for the preprotein than that selected for the recombinant forms (SEQ ID NOS:12, 16, and 20) based on prediction (G. von Heijne et al., *Eur. J. Biochem*. 180:535-545, 1989) combined with homology considerations). Because the size previously determined for the native GPP synthase was 54±3 kDa (D. Tholl et al., *Arch. Biochem. Biophys*. 386:233-242, 2001), these results confirm a homodimeric architecture for this enzyme. This subunit architecture is the same as reported for FPP synthases and GGPP synthases (K. Ogura and T. Koyama, *Chem. Rev.* 98:1263-1276, 1998), and thus typical of other short-chain prenyltransferases, but is markedly different from the unusual heterotetrameric structure of the GPP synthase from *Mentha* (C. Burke and R. Croteau, *J. Biol. Chem.* 277:3141-3149, 2002).

Kinetic characterization of the GPP synthases (SEQ ID NOS:12, 16, and 20). To compare substrate binding behavior and turnover rates of these grand fir GPP synthases (SEQ ID NOS:12, 16, and 20) to those of the *Mentha* synthase, kinetic constants were determined (Table 1).

TABLE 1

APPARENT KINETIC CONSTANTS FOR RECOMBINANT GPP SYNTHASES (SEQ ID NOS: 12, 16, AND 20) FROM GRAND FIR

| Enzyme | $K_M$ | | | $k_{cat}$ |
| --- | --- | --- | --- | --- |
| | IPP[a] μM | DMAPP[b] μM | $MgCl_2$[c] | $s^{-1}$ |
| AgGPPS1 (SEQ ID NO: 16) | 44 ± 5 | 163 ± 13 | 0.8 ± 0.2 | 1.6 ± 0.1 |
| AgGPPS2 (SEQ ID NO: 12) | 55 ± 4 | 90 ± 1 | 0.9 ± 0.1 | 1.8 ± 0.1 |
| AgGPPS3 (SEQ ID NO: 20) | 44 ± 7 | 82 ± 5 | 0.8 ± 0.1 | 0.5 ± 0.1 |

Data are the means ± SD of three determinations.
[a]At saturating concentrations of DMAPP (350 mM).
[b]At saturating concentrations of IPP (212 mM).
[c]At saturating concentrations of IPP and DMAPP.

The apparent $K_M$ values for IPP, DMAPP and $MgCl_2$ for all three synthases (SEQ ID NOS:12, 16, and 20) are comparable to those values of the *Mentha* enzyme, with the exception of $K_{M(DMAPP)}$ for AgGPPS1 (SEQ ID NO:16) which is two-fold higher. The Michaelis constants are also 4 to 10-fold higher than those reported previously for the partially purified GPP synthase from grand fir stems (D. Tholl et al., *Arch. Biochem. Biophys*. 386:233-242, 2001). All three isoforms (SEQ ID NOS:12, 16, and 20) were inhibited at $MgCl_2$ concentrations greater than 4 mM; this phenomenon was not observed with the *Mentha* GPP synthase. Both AgGPPS1 (SEQ ID NO:16) ($k_{cat}$=1.6 $s^{-1}$) and AgGPPS2 (SEQ ID NO:12) ($k_{cat}$=1.8 $s^{-1}$) had four fold higher turnover rates than AgGPPS3 (SEQ ID NO:20) ($k_{cat}$=0.47 $s^{-1}$). The turnover rate for AgGPPS2 (SEQ ID NO:12) (the highest of the three isoforms) is three-fold lower than that of the heterotetrameric *Mentha* GPP synthase ($k_{cat}$=4.8 $s^{-1}$); however, it is likely that the latter (a dimer of heterodimers) has two functional active sites (C. C. Burke et al., *Proc. Natl. Acad. Sci. USA* 96:13062-13067, 1999), which would yield a more comparable $k_{cat}$ of 2.4 $s^{-1}$ per site relative to the homodimeric forms. It is worth noting that the heterodimeric GPP synthase constructs prepared by coupling the *Mentha* GPP synthase small subunit with the *Taxus* GGPP synthase and the *Abies* GGPP synthase yielded turnover rates of about 2.5 $s^{-1}$ (C. Burke and R. Croteau, *J. Biol. chem.* 277:3141-3149, 2002). These kinetic comparisons indicate that the catalytic efficiencies per functional dimer are roughly the same for GPP synthases of homodimeric, heterodimeric and heterotetrameric architectures. However, for the purpose of metabolic engineering of monoterpene biosynthesis, the homodimeric GPP synthase types are clearly superior to the heteromeric forms in allowing single gene transformations with this prenyltransferase to alter flux at this central branchpoint of isoprenoid metabolism.

EXAMPLE 2

This example describes a hybridization protocol that can be used to identify isolated nucleic acid molecules that each encode a geranyl diphosphate synthase protein, wherein each isolated nucleic acid molecule hybridizes to a nucleic acid molecule consisting of the sequence set forth in SEQ ID NO:1 under conditions of 5×SSC at 45° C. for one hour.

Hybridization solution should preferably be prepared and filtered through a 0.45 micron disposable cellulose acetate filter. The composition of the hybridization solution is 5×SSC, 5×Denhardt's reagent, 0.5% sodium dodecyl sulfate (SDS), 100 μg/ml denatured, fragmented salmon sperm DNA.

Denhardt's reagent is utilized in nucleic acid hybridization solutions. 500 ml of 50×Denhardt's reagent (the 50-fold concentrate) includes 5 g Ficoll (Type 400, Pharmacia), 5 g polyvinylpyrrolidone, 5 g bovine serum albumin (Fraction V, Sigma) and water to a final volume of 500 ml.

The nitrocellulose filter or nylon membrane containing the target DNA is floated on the surface of a tray of 5×SSC until it becomes thoroughly wetted from beneath. The filter is submerged for 2 minutes. The wet filter is slipped into a heat-sealable bag. 0.2 ml of hybridization solution is added for each square centimeter of nitrocellulose filter or nylon membrane.

As much air as possible is squeezed from the bag. The open end of the bag is sealed with a heat sealer. The bag is incubated for 1-2 hours submerged at the desired temperature (typically no higher than the hybridization temperature). It is desirable to agitate the bag.

If the radiolabeled probe is double-stranded, it is denatured by heating for 5 minutes at 100° C. Single-stranded probe need not be denatured. The denatured probe is chilled rapidly in ice water. Ideally, probe having a specific activity of $10^9$ cpm/μg, or greater, should be used. Hybridization is carried out for the desired time period at 50° C., typically using 1-2 μg/ml radiolabeled probe.

The bag containing the filter is removed from the water bath. The bag is opened by cutting off one corner with scissors. The denatured probe is added to the hybridization solution, and then as much air as possible is squeezed from the bag. The bag is resealed with the heat sealer so that as few bubbles as possible are trapped in the bag. To avoid radioactive contamination of the water bath, the resealed bag should be sealed inside a second, noncontaminated bag.

The bag is incubated submerged in a water bath for the required period of hybridization (for example, 16 hours) at 45° C. The bag is removed from the water bath and one corner is cut off. The hybridization solution is poured into a container suitable for disposal, and then the bag is cut along the length of three sides. The filter is removed and immediately submerged in a tray containing several hundred milliliters of 2×SSC and 0.5% SDS at room temperature (no higher than 25° C.). The filter should not be allowed to dry out at any stage during the washing procedure.

After 5 minutes, the filter is transferred to a fresh tray containing several hundred milliliters of 2×SSC and 0.1%

SDS and incubated for 15 minutes at room temperature (no higher than 25° C.) with occasional gentle agitation. The filter should then be washed at the desired stringency, i.e., in the desired concentration of SSC and at the desired temperature. If, for example, nucleic acid molecules that hybridize to the probe at a temperature of 45° C. in 5×SSC are sought, then the filter is washed in 5×SSC at 45° C., i.e., nucleic acid molecules that do not hybridize to the probe under conditions of 5×SSC at 45° C. are washed off. Washing can be done for any desired time period, such as one hour, with several changes of washing solution.

After washing remove most of the liquid from the filter by placing it on a pad of paper towels. Place the damp filter on a sheet of Saran Wrap. Apply adhesive dot labels marked with radioactive ink to several asymmetric locations on the Saran Wrap. These markers serve to align the autoradiograph with the filter. Cover the labels with Scotch Tape. This prevents contamination of the film holder or intensifying screen with the radioactive ink. Radioactive ink is made by mixing a small amount of $^{32}$P with waterproof black drawing ink. Use a fiber-tip pen to apply ink to the adhesive labels.

Cover the filter with a second sheet of Saran Wrap, and expose the filter to X-ray film (Kodak XAR-2 or equivalent) to obtain an autoradiographic image. The exposure time should be determined empirically.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule comprising a sequence of nucleotides selected from the group consisting of:
   (a) the nucleotide sequence set forth in SEQ ID NO:2;
   (b) a nucleotide sequence having at least 99% identity to SEQ ID NO:2;
   (c) the nucleotide sequence set forth in SEQ ID NO:9; and
   (d) a nucleotide sequence having at least 99% identity to SEQ ID NO:9;
wherein said molecule encodes a protein having geranyl diphosphate synthase activity.

2. The isolated nucleic acid molecule of claim 1 comprising a sequence of nucleotides selected from the group consisting of SEQ ID NO:2 and a nucleotide sequence having at least 99% identity to SEQ ID NO:2.

3. The isolated nncleic acid molecule of claim 1 comprising a sequence of nucleotides selected from the group consisting of SEQ ID NO:9 and a nucleotide sequence having at least 99% identity to SEQ ID NO:9.

4. The isolated rmcleic acid molecule of claim 1 comprising the nucleic acid sequence set forth in SEQ ID NO:2.

5. The isolated nucleic acid molecule of claim 1 consisting of the nucleic acid sequence set forth in SEQ ID NO:2.

6. A vector comprising the nucleic acid molecule of claim 1.

7. The vector of claim 6 wherein said vector is an expression vector.

8. An isolated host cell comprising the vector of claim 6.

9. The host cell of claim 8 wherein the host cell is a prokaryotic cell.

10. The host cell of claim 8 wherein the host cell is a eukaryotic cell.

11. The host cell of claim 8 wherein the host cell is a plant cell.

12. The plant cell of claim 11 wherein the plant cell is a cell of a plant of the genus *Abies*.

13. The isolated nucleic acid molecule of claim 1 comprising the nucleic acid sequence set forth in SEQ ID NO:9.

14. The isolated nucleic acid molecule of claim 3 comprising a sequence of nucleotides having at least 99% identity to SEQ ID NO:9.

* * * * *

UNITED STATES PATENT AND TRADEMARK OFFICE
CERTIFICATE OF CORRECTION

PATENT NO. : 7,390,643 B2  
APPLICATION NO. : 11/047828  
DATED : June 24, 2008  
INVENTOR(S) : Rodney Bruce Croteau et al.

Page 1 of 1

It is certified that error appears in the above-identified patent and that said Letters Patent is hereby corrected as shown below:

| COLUMN | LINE | ERROR |
|---|---|---|
| 17 | 60 | "W. Sitthithawom et al." should read --W. Sitthithaworn et al.-- |
| 18 | 28 | "(110%" should read --(~10%-- |
| 79 (Claim 3, | 45 line 1) | "nncleic" should read --nucleic-- |
| 79 (Claim 4, | 49 line 1) | "rmcleic" should read --nucleic-- |

Signed and Sealed this

Seventeenth Day of February, 2009

JOHN DOLL  
*Acting Director of the United States Patent and Trademark Office*